United States Patent [19]

Maignan et al.

[11] Patent Number: 4,826,969

[45] Date of Patent: May 2, 1989

[54] BICYCLIC NAPHTHALENIC DERIVATIVES, A PROCESS FOR PREPARING THE SAME AND HUMAN OR VETERINARY MEDICINES AND COSMETIC COMPOSITIONS CONTAINING SAID DERIVATIVES

[75] Inventors: Jean Maignan, Tremblay les Gonesse; Gérard Lang, Saint Gratien; Gérard Malle, Villiers sur Morin; Serge Restle, Aulnay Sous Bois; Braham Shroot, Antibes, all of France

[73] Assignee: Centre International de Recherches Dermatologiques C.I.R.D., Valbonne, France

[21] Appl. No.: 918,507

[22] Filed: Oct. 14, 1986

[30] Foreign Application Priority Data

Oct. 11, 1985 [FR] France ................... 85 15106
Jul. 9, 1986 [FR] France ................... 86 10020

[51] Int. Cl.⁴ .................... A61K 31/19; A61K 31/12; C07C 63/36; C07C 149/243
[52] U.S. Cl. ......................... 536/55.2; 560/8; 560/100
[58] Field of Search ............... 536/55.2; 514/62, 54; 560/100, 8

[56] References Cited

U.S. PATENT DOCUMENTS 1,917,285 7/1933 Adams et al. ................ 562/460

*Primary Examiner*—Ronald W. Griffin
*Attorney, Agent, or Firm*—Cushman, Darby & Cushman

[57] ABSTRACT

A bicyclic naphthalenic compound has the formula

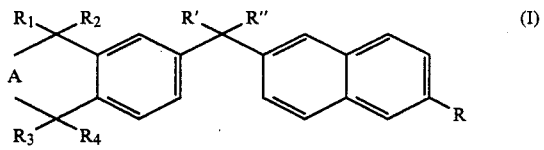

wherein

A represents methylene or dimethylene, substituted or not by lower alkyl, $R_1$, $R_2$, $R_3$ and $R_4$ represent hydrogen or lower alkyl, or $R_1$ and $R_3$ taken together form a methylene or dimethylene bridge when A represents dimethylene, R' represents hydrogen, OH, alkoxy having 1-4 carbon atoms, acyloxy having 1-4 carbon atoms or amino, R" represents hydrogen or alkoxy having 1-4 carbon atoms, or r' and R" taken together form an oxo, methano or hydroxyimino group, R represents —$CH_2OH$ or —$COR_5$, $R_5$ represents hydrogen, —$OR_6$ or

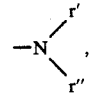

$R_6$ represents hydrogen, alkyl having 1-20 carbon atoms, monohydroxyalkyl, polyhydroxyalkyl, aryl or aralkyl optionally substituted, the residue of a sugar or

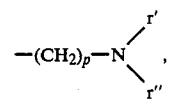

p is 1, 2 or 3, and r' and r", each independently, represent hydrogen, lower alkyl, monohydroxyalkyl optionally interrupted by a heteroatom, polyhydroxyalkyl, aryl or benzyl optionally substituted, the residue of an amino acid, an aminoester or an aminated sugar, or r' and r" together form with the nitrogen atom to which they are attached, a heterocycle substituted or not, and the salts of said compounds of formula (I) or the optional isomers thereof.

30 Claims, No Drawings

BICYCLIC NAPHTHALENIC DERIVATIVES, A PROCESS FOR PREPARING THE SAME AND HUMAN OR VETERINARY MEDICINES AND COSMETIC COMPOSITIONS CONTAINING SAID DERIVATIVES

The present invention relates to new bicyclic naphthalenic derivatives, to a process for their preparation and to their use in human or veterinary medicine and in cosmetic compositions.

The compounds according to the present invention exhibit an activity in the topical and systemic treatment of dermatologic diseases linked to a keratinization disorder (differentiation-proliferation) and dermatologic diseases (or others) having inflammatory and/or immunoallergic components and in the treatment of illnesses of the degeneration of conjunctive tissue as well as an anti-tumor activity.

Moreover, these compounds can be employed in the treatment of atrophy, be it cutaneous or respiratory, and in rheumatoid psoriasis.

These compounds also possess good activity against the germs involved in acne.

Finally, the compounds of the present invention are usefully employed in the ophthamalogy field, principally in the treatment of corneopathies.

The bicyclic naphthalenic derivatives according to the present invention can be represented by the formula:

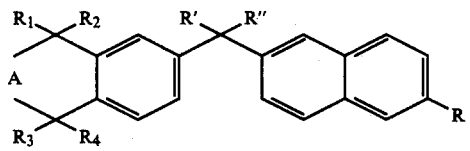

wherein
A represents methylene or dimethylene, substituted or not by lower alkyl,
$R_1$, $R_2$, $R_3$ and $R_4$, each independently, represent hydrogen or lower alkyl having 1–6 carbon atoms, or
$R_1$ and $R_3$ taken together form a methylene or dimethylene bridge when A represents dimethylene,
R' represents hydrogen, OH, alkoxy having 1–4 carbon atoms, acyloxy having 1–4 carbon atoms or amino,
R" represents hydrogen or alkoxy having 1–4 carbon atoms,
or R' and R" taken together form an oxo radical (=O), a methano radical ($=CH_2$) or a hydroxyimino radical (=N—OH),
R represents —$CH_2OH$ or —$COR_5$,
$R_5$ represents hydrogen, $OR_6$ or

$R_6$ represents hydrogen, alkyl having 1–20 carbon atoms, monohydroxyalkyl, polyhydroxyalkyl, aryl or aralkyl optionally substituted, or the residue of a sugar or even

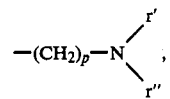

p is 1, 2 or 3, and
r' and r" each independently represent hydrogen, lower alkyl, monohydroxyalkyl optionally interrupted by a heteroatom, polyhydroxyalkyl, aryl or benzyl optionally substituted, the residue of an amino acid, an aminoester or an aminated sugar, or together form with the nitrogen atom to which they are attached, a substituted or unsubstituted heterocycle,
and the salts of said compounds of formula I as well as their optical isomers.

By lower alkyl is meant an alkyl radical having 1–6 carbon atoms.

Representative lower alkyl radicals and alkyl radicals having up to 20 carbon atoms include methyl, ethyl, propyl, isopropyl, butyl, tert. butyl, 2-ethylhexyl, octyl, isooctyl, dodecyl, hexadecyl and octadecyl radicals.

By monohydroxyalkyl is meant a radical having 2–6 carbon atoms and principally 2-hydroxy ethyl, 2-hydroxy propyl or 2'-hydroxy-2-ethoxyethyl.

By polyhydroxyalkyl is meant a radical containing 3–6 carbon atoms and 2–5 hydroxy groups such as 2,3-dihydroxypropyl, 1,3,-dihydroxy-2-propyl or the residue of pentaerythritol.

Representative alkoxy radicals having 1–4 carbon atoms include methoxy, isopropoxy, butoxy or tert. butoxy.

By aryl is meant phenyl optionally substituted by at least one of halogen, —OH, —$NO_2$, lower alkyl, trifluoromethyl or a carboxylic acid function.

Representative preferred aralkyl radicals include benzyl as well as phenethyl radicals.

By residue of a sugar is meant a residue derived from, for example, glucose, mannose, erythrose or galactose.

Representative residues of aminated sugars include those derived from glucosamine, galactosamine, mannosamine or meglumine.

When the radical r' and r" taken together form with the nitrogen atom to which they are attached, a heterocycle, the heterocycle is, preferably, piperidino, piperazino, morpholino, pyrrolidino or 4-(2'-hydroxyethyl) piperazino.

When the compounds according to the present invention are provided in the form of salts, they can be salts of an alkali or alkaline earth metal or even of zinc, or of an organic amine when they carry at least one free acid function, or of salts of a mineral or organic acid principally the hydrochloride, hydrobromide or citrate when they carry at least one amine function.

Representative compounds of formula I which are particularly preferred according to the present invention include those corresponding to the following formulas II, III and IV:

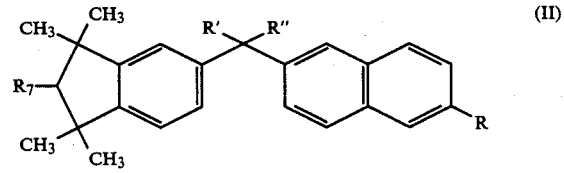

wherein
R' represents hydrogen or OH,
R" represents hydrogen, or
R' and R" taken together form an oxo radical (=O),
R represents CH$_2$OH or —COOR$_6$,
R$_6$ represents hydrogen or alkyl having 1-6 carbon atoms, and
R$_7$ represents hydrogen or methyl.

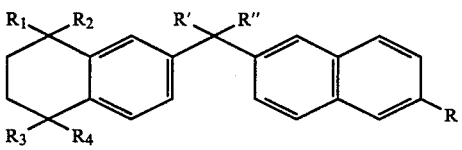

wherein
R$_1$, R$_2$, R$_3$ and R$_4$ represent —CH$_3$,
R' represents hydrogen, OH, alkoxy having 1-4 carbon atoms or acyloxy having 1-4 carbon atoms,
R" represents hydrogen, or
R' and R" taken together form an oxo radical (=O) or a methano radical (=CH$_2$),
R represents —CH$_2$OH or —COR$_5$,
R$_5$ represents hydrogen, —OR$_6$ or

R$_6$ represents hydrogen or alkyl having 1-6 carbon atoms, and
r' and r" each independently represent hydrogen, alkyl having 1-6 carbon atoms, 4-hydroxyphenyl, 2'-hydroxyethoxyethyl or 1-carboxy-3-methylthiopropyl.

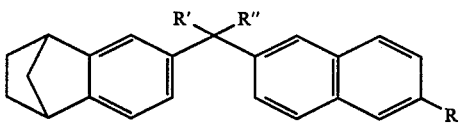

wherein
R' and R" taken together form an oxo radical (=O),
R represents —COR$_5$,
R$_5$ represents —OR$_6$ or

R$_6$ represents hydrogen or alkyl having 1-6 carbon atoms, and
r' and r" each independently represent hydrogen or alkyl having 1-6 carbon atoms.

Representative compounds of formula I according to the present invention include the following:
(1) 6-[(1,1,3,3, tetramethyl-5-indanyl)carbonyl]2-methyl naphthalene carboxylate,
(2) 6-[(1,1,3,3, tetramethyl-5-indanyl)carbonyl]2-naphthalene carboxylic acid,
(3) 6-[(1,1,2,3,3, pentamethyl-5-indanyl)carbonyl]2-methyl naphthalene carboxylate,
(4) 6-[(1,1,2,3,3, pentamethyl-5-indanyl)carbonyl]2-naphthalene carboxylic acid,
(5) 6-[(1,1,2,3,3, pentamethyl-5-indanyl)hydroxymethyl]2-naphthalene carboxylic acid,
(6) 6-[(5,5,8,8-tetramethyl-5,6,7,8-tetrahydro-2-naphthyl)hydroxymethyl]2-naphthalene carboxylic acid,
(7) N-ethyl 6-[(5,5,8,8-tetramethyl-5,6,7,8-tetrahydro-2-naphthyl)hydroxymethyl]2-naphthalene carboxamide,
(8) 1-[(5,5,8,8-tetramethyl-5,6,7,8-tetrahydro-2-naphthyl)-1-(6-carboxy-2-naphthyl)methane,
(9) N-ethyl 6-[(1,1,3,3-tetramethyl-5-indanyl)carbonyl]2-naphthalene carboxamide,
(10) N-ethyl 6-[(1,1,2,3,3-pentamethyl-5-indanyl)carbonyl]2-naphthalene carboxamide,
(11) N-ethyl 6-[(1,1,2,3,3-pentamethyl-5-indanyl)hydroxymethyl]-2-naphthalene carboxamide,
(12) 6-[(5,5,8,8-tetramethyl-5,6,7,8-tetrahydro-2-naphthyl)acetoxymethyl]2-naphthalene carboxylic acid,
(13) 6-[2-(5,5,8,8-tetramethyl-5,6,7,8-tetrahydro-2-naphthyl)2-ethenyl]2-methyl naphthalene carboxylate,
(14) 6-[2-(5,5,8,8-tetramethyl-5,6,7,8-tetrahydro-2-naphthyl)-2-ethenyl]2-naphthalene carboxylic acid,
(15) 6-[(5,5,8,8-tetramethyl-5,6,7,8-tetrahydro-2-naphthyl)hydroxymethyl]2-naphthalene carbinol,
(16) 6-[(5,5,8,8-tetramethyl-5,6,7,8-tetrahydro-2-naphthyl)butoxymethyl]2-naphthalene carbinol,
(17) 6-[(5,5,8,8-tetramethyl-5,6,7,8-tetrahydro-2-naphthyl)butoxymethyl]2-naphthalene carboxylic acid,
(18) 6-[(5,5,8,8-tetramethyl-5,6,7,8-tetrahydro-2-naphthyl)hydroxymethyl]2-naphthaldehyde,
(19) 6-[(5,5,8,8-tetramethyl-5,6,7,8-tetrahydro-2-naphthyl)hydroxyiminomethyl]2-ethyl naphthalene carboxylate,
(20) 6-[(5,5,8,8-tetramethyl-5,6,7,8-tetrahydro-2-naphthyl)hydroxyiminomethyl]2-naphthalene carboxylic acid,
(21) N-ethyl 6-[(5,5,8,8-tetramethyl-5,6,7,8-tetrahydro-2-naphthyl)hydroxyiminomethyl]2-naphthalene carboxamide,
(22) 6-[(5,5,8,8-tetramethyl-5,6,7,8-tetrahydro-2-naphthyl)aminomethyl]2-ethyl naphthalene carboxylate,
(23) 6-[(5,5,8,8-tetramethyl-5,6,7,8-tetrahydro-2-naphthyl)aminomethyl]2-naphthalene carboxylic acid,
(24) 6-[(5,5,8,8-tetramethyl-5,6,7,8-tetrahydro-2-naphthyl)carbonyl]2-naphthalene carboxylic acid and its methyl ester,
(25) N-ethyl 6-[(5,5,8,8-tetramethyl-5,6,7,8-tetrahydro-2-naphthyl)carbonyl]2-naphthalene carboxamide,
(26) 6-[(5,5,8,8-tetramethyl-5,6,7,8-tetrahydro-2-naphthyl)carbonyl]2-naphthalene carboxaldehyde,
(27) 6-[(5,5,8,8-tetramethyl-5,6,7,8-tetrahydro-2-naphthyl)carbonyl]2-naphthalene carbinol,
(28) N(2'-hydroxy-2-ethoxyethyl)6-[5,5,8,8-tetramethyl-5,6,7,8-tetrahydro-2-naphthyl)carbonyl]2-naphthalene carboxamide,
(29) N-p-hydroxyphenyl 6-[(5,5,8,8-tetramethyl-5,6,7,8-tetrahydro-2-naphthyl)carbonyl]2-naphthalene carboxamide,
(30) N-(1-ethoxycarbonyl-3-methylthiopropyl)6-[(5,5,8,8-tetramethyl-5,6,7,8-tetrahydro-2-naphthyl)-carbonyl]2-naphthalene carboxamide,
(31) N-(1-carboxy-3-methylthiopropyl)6-[(5,5,8,8-tetramethyl-5,6,7,8-tetrahydro-2-naphthyl)carbonyl]2-naphthalene carboxamide,
(32) 6-[(5,8-methano-5,6,7,8-tetrahydro-2-naphthyl)carbonyl]2-naphthalene carboxylic acid and its methyl ester,
(33) 6-[(5,6,7,8-tetrahydro-2-naphthyl)carbonyl]2-naphthalene carboxylic acid and its methyl ester, and

(34) N-ethyl 6-[(5,6,7,8-tetrahydro-2-naphthyl)carbonyl]2-naphthalene carboxamide.

The present invention also relates to a process for preparing the compounds of formula I.

These compounds can be obtained in accordance with various methods as a function of their structure. They are preferably produced in accordance with the following reaction scheme:

ramethyl tetraline) is preapred in accordance with the method described by H. Q. Brunson and J. W. Kroger, J. Am. Chem. Soc. 62, 36–44 (1940). The 5,8-methano-5,6,7,8-tetrahydro naphtalene is obtained in accordance with the method described in J. Org. Chem., 32 893–901 (1967). The 1,1,2,3,3-pentamethyl indane and the 1,1,3,3-tetramethyl indane are obtained in accordance with the methods described in French Pat. No.

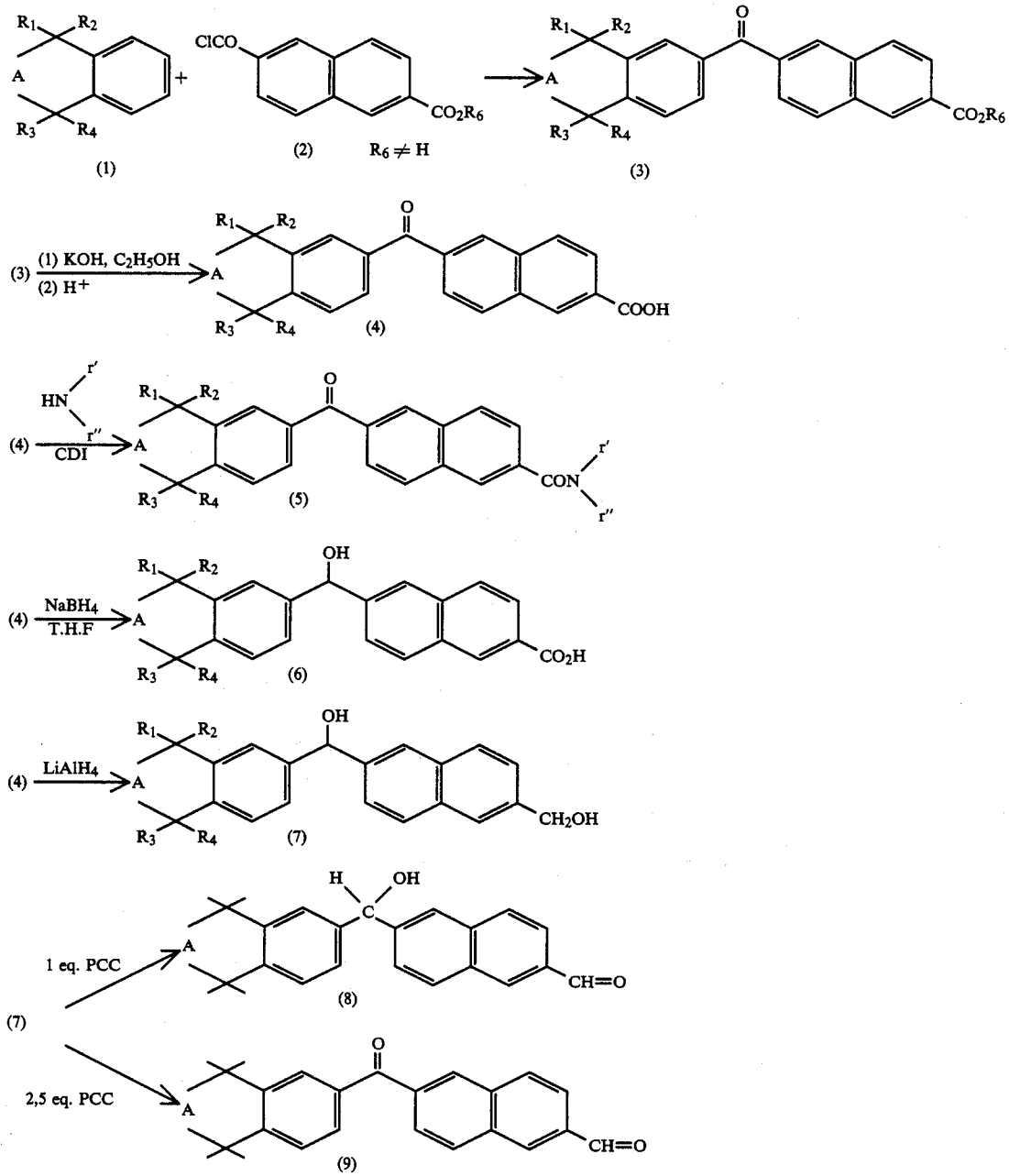

The chloride of 6-alkoxycarbonyl-2-naphthalene carboxylic acid (2) is obtained by the monosaponification reaction of a 2,6-alkyl naphthalene dicarboxylate and the formation of the chloride by the action of thionyl chloride in accordance with known methods for the preparation of acid chlorides.

Among the initial reactants of formula (1) tetraline and indane are commercial products. 5,5,8,8-tetramethyl-5,6,7,8-tetrahydro naphthalene (or 5,5,8,8-tet- 1,392,804.

The condensation reaction of the 6-alkoxy carbonyl 2-naphthalene carboxylic acid chloride (2) on the bicyclic aromatic compound (1) is carried out under conventional Friedel-Crafts reaction conditions, that is, in the presence of anhydrous aluminum chloride or stannous chloride in 1,2-dichloroethane at a temperature between 0° C. and 25° C., wtih stirring.

Starting with the keto ester (3) there is produced, by saponification, the corresponding keto-acid (4) which can then be transformed into the amide of formula (5) by the action of an amine of the formula tion in accordance with the following reaction scheme:

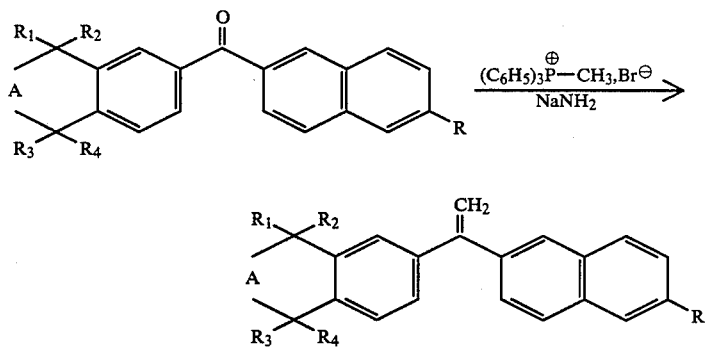

(r' and r" having the same meanings as those given above) in the presence of N,N'-carbonyl diimidazole (CDI).

When $R_6$ represents a monohydroxy or poly-hydroxy radical, it is preferable to prepare the keto-acid (4) starting with the methyl ester (3) ($R_6$=$CH_3$) and then esterfy the keto-acid thus obtained into the keto-ester of the selected mono- or polyhydric alcohol in accordance with known procedures.

Starting with the keto-acid (4) the reduction by sodium borohydride in an organic solvent such as THF provides the secondary alcohol (6) and the reduction by aluminum lithium hydride of the keto-acid (4) produces the diol (7).

On oxidation of the diol (7) by one equivalent of pyridinium chlorochromate (PCC), there is produced the aldehyde alcohol (8); when using at least 2 equivalents of PCC the ketoaldehyde (9) is produced.

The compounds according to the present invention wherein R'=R"=H are obtained by reduction with zinc of the ketonic derivatives in acetic acid in the presence of HCl.

The reduction reactions of the carbonyl must, however, be compatible with the nature of the R group. It can be desirable to ensure eventual protection, however, the reduction of the carbonyl raises no difficulty when R=$CO_2H$.

The acyloxy derivatives of the compounds of formula (I), (R'=$C_1$-$C_4$ acyloxy and R"=H) are obtained by reacting an activated form of the acid, such as an anhydride or acid chloride with a compound according to the invention in which R'=OH and R"=H.

The alkoxy derivatives of the compounds of formula (I), (R'=$C_1$-$C_4$ alkoxy and R"=H) are obtained in the same way starting with compounds of formula (I), (R'=OH and R"H), in accordance with known methods.

For the preparation of acyloxy and alkoxy derivatives, it is preferable that the radical R be an ester, an acid or an amide function.

The compounds of formula (I) in which R' and R"=methano (=$CH_2$) are obtained by the Wittig reac- The compounds of formula (I) wherein R' and R"=hydroxyimino (=N—OH) are obtained by the action of hydroxylamine hydrochloride on corresponding carbonyl compounds, in an organic solvent, such as ethanol in the presence of a mineral base such as sodium bicarbonate or an organic base such as triethylamine. These hydroxyimino derivatives lead on reduction with zinc, in an acetic medium, to amines of formula (I) in which R'=$NH_2$ and R"=H.

The present invention further relates to a medicine comprising the compounds of formula (I) as defined above.

These compounds exhibit excellent activity in the inhibition test or ornithine decarboxylase in nude rats after induction, by "tape stripping", M. Bouclier et al, Dermatologica 169, No. 4 (1984). This test is recognized as a measure of an antiproliferative activity.

These compounds are particularly appropriate for treating dermatologic ailments linked to a keratinization disorder (differentiation-proliferation) as well as dermatologic diseases, or others, having an inflammatory and/or immunoallergic component principally:

acne vulgaris, comedons or polymorphs, solar senile acne and medicinal or professional acne, extensive and/or severe forms of psoriasis and other keratinization disorders, and principally ichtysoses and ichtysois-like conditions, Darier malady, palmo-plantar keratodermies, leucophasies and leucophasie-like states, lichen plan, all malignant or benign dermatologic proliferations, severe or extensive.

They are also active in the treatment of tumors, of rheumatoid psoriasis, cutaneous or respiratory atrophies as well as in certain ophthalomogic problems relating to corneophathies.

These compounds also possess good activity on germs implicated in acne.

Thus, the present invention also relates to medicinal compositions containing at least one compound of formula (I), such as defined above, or one of its salts or one of its optical isomers.

The present invention thus relates to a new medicinal composition, intended principally for the treatment of the above-mentioned disorders, comprising in a pharmaceutically acceptable support, an effective amount of at least one compound of formula (I) and/or one of its salts and/or one of its optical isomers.

The compounds according to the present invention are generally administered at a daily dosage of about 2 μg/kg to 2 mg/kg of body weight.

As the vehicle or carrier for these compositions, any conventional vehicle can be employed, the active component being found either in the dissolved state, or in the dispersed state in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered paranterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotions, gels, sprays or suspensions.

These compositions for topical administration can be provided under anhydrous form or in aqueous form according to clinical indications.

When administered ocularly, the composition is provided principally in the form of an eyewash.

The compositions for topical or ocular administration contain preferably from 0.0005 to about 5 percent by weight of at least one compound of formula (I) such as defined above, relative to the total weight of the composition.

The compounds of formula (I), according to the present invention, are also useful in the cosmetic field, in particular in body and hair hygiene compositions and principally for the treatment of skin having acne tendencies, to improve the growth of hair, to combat hair loss, to combat aganst an oily appearance of the skin or hair, in the prevention or treatment of the harmful effects on the sun or in the treatment of physiologically dry skin.

The present invention thus relates to a cosmetic composition containing, in a cosmetically acceptable vehicle, an effective amount of at least one compound of formula (I) or one of its salts and/or one of its isomers, this composition being provided principally in the form of a lotion, gel, cream, soap or shampoo.

The concentration of the compound of formula (I) in these cosmetic compositions is between 0.0005 and 2 percent by weight and, preferably between 0.01 and 1 percent by weight based on the total weight of the composition.

The medicinal and cosmetic compositions according to the present invention can contain inert or even pharmacodynamic or cosmetically active additives and principally: hydrating agents such as thiamorpholinone and its derivatives or urea; antiseborrheic or anti-acne agents such as S-carboxymethylcysteine, S-benzyl cysteamine, their salts and their derivatives, tioxolone or benzoyl peroxide; antibiotics such as erythromycin and its esters, neomycin, tetracyclines and 4,5-polymethylene-3-isothiazolones; agents promoting the growth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and phenytoin (5,5-diphenyl-2,4-imidazolidine dione); steroidal or non-steroidal anti-inflammatory agents; carotenoids and, principally, β-carotene; anti-psoriasic agents such as anthralin and its derivatives and 5,8,11,14-eicosatetraynoic and 5,8,1-eicosatriynoic acids.

The compositions according to the present invention can also contain flavor improving agents, preservatives, stabilizers, humidity regulating agents, pH regulating agents, osmotic pressure modifying agents, emulsifiers, UV-A and UV-B filters, anti-oxidants such as α-tocopherol, butyl hydroxy anisol or butyl hydroxy toluene.

The following non-limiting examples illustrate the preparation of the active compounds of formula (I) according to the present invention as well as compositions containing these compounds.

EXAMPLE I

Preparation of
6-[(1,1,3,3-tetramethyl-5-indanyl)carbonyl] 2-methylnaphthalene carboxylate Compound of formula II wherein R' and R"=oxo, $R_7$=H and R=—$CO_2CH_3$ To a suspension of 2.26 g (13 mmoles) of 1,1,3,3-tetramethyl indane and 3.23 g (13 mmoles) of 6-methoxycarbonyl-2-naphthalene carboxylic acid chloride in 80 cm$^3$ of anhydrous 1,2-dichloroethane, there are added, in portions, 3.33 g (25 mmoles) of anhydrous aluminum chloride. The mixture is stirred for 5 hours at ambient temperature, then poured into 100 cm$^3$ of ice water. The organic phase is decanted and the aqueous phase is extracted twice with 100 cm$^3$ of dichloroethane. The dichloroethane phases are combined, washed with sodium bicarbonate, dried on sodium sulfate, then concentrated under reduced pressure. The resulting solid is taken up in 100 cm$^3$ of methanol, filtered and then recrystallized in 250 cm$^3$ of methanol. After filtering and drying under a vacuum 3.4 g of pale yellow flakes of 6-[(1,1,3,3-tetramethyl-5-indanyl)carbonyl] 2-methyl naphthalene carboxylate, having a melting point of 135° C., are obtained.

NMR $^1$H spectrum 60 MHz conforms to the expected structure.

Elemental analysis: $C_{26}H_{26}O_3$: Calculated: C 80,80, H 6.78, O 12.42. Found: C 80.75, H 6.82, O 12.69.

EXAMPLE II

Preparation of
6-[(1,1,3,3-tetramethyl-5-indanyl)carbonyl] 2-naphthalene carboxylic acid Compound of formula II wherein R' and R"=oxo, $R_7$=H and R=—$CO_2H$ A suspension of 1.4 g (3.6 mmoles) of 6-[(1,1,3,3-tetramethyl-5-indanyl)carbonyl] 2-methyl naphthalene carboxylate, obtained in Example I, is stirred for 2 hours 30 minutes in a mixture of 25 cm$^3$ of alcohol and 25 cm$^3$ of 6N aqueous potash heated at reflux. After the addition of 80 cm$^3$ of water, the alcohol is removed by evaporation under a vacuum. The resulting aqueous phase is diluted to 250 cm$^3$, cooled to a temperature between 0° and +5° C. and then acidified with 20 cm$^3$ of 12N HCl. The resulting precipitate is filtered, washed with water and dried on a potash at 80°-100° C. After recrystallization in methanol and treatment with animal charcoal, 1.06 g of white crystals of 6-[(1,1,3,3-tetramethyl-5-indanyl)carbonyl] 2-naphthalene carboxylic acid, having a melting point of 231°-2° C., are obtained.

NMR $^1$H spectrum 80 MHz conforms to the expected structure.

Elemental analysis: $C_{25}H_{24}O_3$: Calculated: C 80.62, H 6.50, O 12.89. Found: C 80.71, H 6.44, O 12.84.

EXAMPLE III

Preparation of 6-[(1,1,2,3,3-pentamethyl-5-indanyl)carbonyl] 2-methyl naphthalene carboxylate Compound of formula (II) wherein R' and R"=oxo, $R_7=CH_3$ and R=—$CO_2CH_3$ To a suspension of 2.47 g (13 mmoles) of 1,1,2,3,3-pentamethyl indane and 3.23 g (13 mmoles) of 6-methoxycarbonyl-2-naphthalene carboxylic acid chloride in 80 cm$^3$ of anhydrous 1,2,-dichloroethane, there are added in portions, over a 1 hour period, 3.33 g (25 mmoles) of anhydrous aluminum chloride. The mixture is stirred for 5 hours at ambient temperature and then poured into 100 cm$^3$ of ice water. The organic phase is decanted and the aqueous phase extracted twice with 100 cm$^3$ of dichloroethane. The dichloroethane phases are combined, washed with sodium bicarbonate, dried on sodium sulfate and then concentrated under reduced pressure. The resulting solid is taken up in 60 cm$^3$ of methanol, filtered, dried and then purified by chromatography on silica gel 60 in a hexane/toluene/ether mixture, 50/20/30, respectively. After evaporation and drying under a vacuum at 80° C., 3 g of white powder of 6-[(1,1,2,3,3-pentamethyl-5-indanyl)carbonyl] 2-methyl naphthalene carboxylate, having a melting point of 139°-141° C., are obtained.

NMR $^1$H spectrum 60 MHz conforms to the expected structure.

Elemental analysis: $C_{27}H_{28}O_3$: Calculated: C 80.97, H. 7.05, O 11.98. Found: C 81.09, H 7.14, O 12.07.

EXAMPLE IV

Preparation of 6-[(1,1,2,3,3-pentamethyl-5-indanyl)carbonyl] 2-naphthalene carboxylic acid Compound of formula (II) wherein R' and R"=oxo, $R_7=$—$CH_3$ and R=—$CO_2H$ A suspension of 2 g (5 mmoles) of 6-[(1,1,2,3,3-pentamethyl-5-indanyl)carbonyl] 2-methyl naphthalene carboxylate, obtained in Example III, is stirred for 2 hours 30 minutes in a mixture of 30 cm$^3$ of alcohol and 30 cm$^3$ of 6N aqueous potash heated at reflux. After addition of 150 cm$^3$ of water, the alcohol is removed by evaporation under a vacuum and the aqueous phase is then diluted to 500 cm$^3$. After cooling to a temperature between 0° and 5° C., the reaction mixture is acidified by the addition of 20 cm$^3$ of 12N HCl. The resulting precipitate is filtered, washed with water and dried on potash at 80°-100° C. After recrystallization in a hexane/acetone mixture, 1.5 g of flocculent white crystals of 6-[(1,1,2,3,3-pentamethyl-5-indanyl)carbonyl] 2-naphthalene carboxylic acid, having a melting point of 237°-8° C., are obtained.

NMR $^1$H spectrum 250 MHz conforms to the expected structure.

Elemental analysis: $C_{26}H_{26}O_3$: Calculated: C 80.80, H 6.78, O 12.42. Found: C 80.86, H 6.77, O 12.30.

EXAMPLE V

Preparation of 6-[(1,1,2,3,3-pentamethyl-5-indanyl)hydroxymethyl] 2-naphthalene carboxylic acid Compound of formula (II) wherein R'=OH, R"=H, $R_7=$—$CH_3$ and R=—$CO_2H$ To a solution of 0.7 g (1.8 mmoles) of 6-[(1,1,2,3,3-pentamehtyl-5-indanyl)carbonyl] 2-naphthalene carboxylic acid, obtained in Example IV, in 25 cm$^3$ of anhydrous tetrahydrofuran, there are added in portions over a 15 minute period, 205 mg (5.4 mmoles) of sodium borohydride. The reaction mixture is stirred overnight at ambient temperature. Once the reduction is completed, the reaction mixture is cooled to a temperature between 0° to 5° C., then slowly acidified by the addition of 0.1N HCl. After extraction with ethyl ether, the ether phase is washed with water, dried on sodium sulfate and evaporated to dryness. After recrystallization of the resulting crude product in a hexane/acetone mixture, 0.55 g of white crystals of 6-[(1,1,2,3,3-pentamethyl-5-indanyl)hydroxymethyl] 2-naphthalene carboxylic acid, having a melting point of 215°-7° C., is obtained.

NMR $^1$H spectrum 250 MHz conforms to the expected structure.

Elemental analysis: $C_{26}H_{28}O_3$: Calculated: C 80.38, H 7.26, O 12.36. Found: C 80.61, H 7.32, O 12.04.

EXAMPLE VI

Preparation of 6-[5,5,8,8-tetramethyl-5,6,7,8-tetrahydro-2-naphthyl) carbonyl] 2-methyl naphthalene carboxylate Compound of formula III wherein $R_1=R_2=R_3=R_4=$—$CH_3$, R' and R"=oxo and R=—$CO_2CH_3$ To a suspension of 1.5 g (11.2 mmoles) of anhydrous aluminum chloride in 10 cm$^3$ of anhydrous dichloromethane, there is slowly added a solution of 1.88 g (10 mmoles) of 1,2,3,4-tetrahydro-1,1,4,4-tetramethyl naphthalene and 2.49 g (10 mmoles) of 6-methoxycarbonyl-2-naphthalene carboxylic acid chloride in 60 cm$^3$ of anhydrous dichloromethane. The mixture is stirred for 4 hours at ambient temperature and then poured into 100 cm$^3$ of acidulated ice water. The organic phase is decanted and the aqueous phase is extracted once with 100 cm$^3$ of dichloromethane. The methylene chloride phases are combined, washed with sodium bicarbonate, dried on sodium sulfate and then concentrated. 3.9 g of a yellow liquid, which crystallizes at ambient temperature, are obtained. This solid is washed with methanol and then recrystallized in 70 cm$^3$ of isopropanol.

2.1 g of 6-[(5,5,8,8-tetramethyl-5,6,7,8-tetrahydro-2-naphthyl)carbonyl] 2-methyl naphthalene carboxylate are obtained.

The isopropanol is evaporated; the resulting solid is washed with a minimum of methanol and then recrystallized in this solvent. A second fraction of 0.7 g of the expected product, identical to that previously obtained, in the form of white crystals whose melting point is 134° C. is thereby recovered.

NMR $^1$H spectrum 60 MHz conforms to the expected structure.

Elemental analysis: $C_{27}H_{28}O_3$: Calculated: C 80.97, H 7.05, O 11.98. Found: C 80.85, H 7.00, O 12.02.

EXAMPLE VII

Preparation of
6-[(5,5,8,8-tetramethyl-5,6,7,8-tetrahydro-2-naphthyl)-
carbonyl] 2-naphthalene carboxylic acid Compound of formula III wherein
$R_1=R_2=R_3=R_4=$ —$CH_3$, R' and R"=oxo and
R= —$CO_2H$ A suspension of 2.5 g of 6-[(5,5,8,8-tetramethyl-5,6,7,8-tetrahydro-2-naphthyl)carbonyl] 2-methyl naphthalene carboxylate, obtained in Example VI, is stirred for 3 hours in a mixture of 30 cm³ of methanol and 30 cm³ of 6N aqueous potash at a temperature between 50° and 60° C. The reaction mixture is then left overnight at ambient temperature. After having added 40 cm³ of water, the methanol is removed by evaporation under a vacuum. The resulting aqueous phase is cooled to a temperature between 0° and 5° C., and then acidified to pH≃1 by the addition of 6N HCl. The resulting precipitate is filtered, washed with water and dried at 80° C. on potash.

After two recrystallizations, one in 40 cm³ of isopropanol, the other in 100 cm³ of methanol, 1.7 g of 6-[(5,5,8,8-tetramethyl-5,6,7,8-tetrahydro-2 naphthyl)carbonyl] 2-naphthalene carboxylic acid are isolated in the form of white crystals whose melting point is 224° C.

NMR ¹H spectrum 250 MHz conforms to the expected structure.

Elemental analysis: $C_{26}H_{26}O_3$: Calculated: C 80.80, H 6.78, O 12.42. Found: C 80.57, H 6.93, O 12.50.

EXAMPLE VIII CL Preparation of N-ethyl 6-[(5,5,8,8-tetramethyl-5,6,7,8-tetrahydro-2-naphthyl)-carbonyl] 2-naphthalene carboxamide Compound of formula III wherein
$R_1=R_2=R_3=R_4=$ —$CH_3$, R' and R"=oxo and
R= —$CONHC_2H_5$ To a suspension of 1 g (2.5 mmoles) of 6-[(5,5,8,8-tetramethyl-5,6,7,8-tetrahydro-2-naphthyl)carbonyl] 2-naphthalene carboxylic acid, obtained in Example VII, in 10 cm³ of anhydrous dichloromethane, there is added 0.49 g (3 mmoles) of N,N'-carbonyl diimidazole with stirring at ambient temperature.

$CO_2$ is liberated. After stirring for one hour, 0.17 cm³ (2.6 mmoles) of anhydrous ethylamine is added. One hour later, the initial acid reactant is completely transformed into the corresponding amide.

The reaction medium is then diluted with 20 cm³ of dichloromethane, washed with 20 cm³ of normal NaOH, then with water up to a neutral pH of the wash waters, dried on sodium sulfate and concentrated to dryness.

1 g of a beige solid is obtained which is then recrystallized in an isopropyl ether/acetonitrile mixture. There is thus obtained, after having filtered and dried the crystals, 0.65 g of N-ethyl 6-[(5,5,8,8-tetramethyl-5,6,7,8-tetrahydro-2-naphthyl)carbonyl] 2-naphthalene carboxamide in the form of white crystals having a melting point of 155° C.

NMR ¹H and infra-red spectra correspond to the expected structure.

Elemental analysis: $C_{28}H_{31}NO_2$: Calculated: C 81.32, H 7.56, N 3.39, O 7.74. Found C 81.33, H 7.53, N 3.30, O 7.72.

EXAMPLE IX

Preparation of
6-[(5,5,8,8-tetramethyl-5,6,7,8-tetrahydro-2-naphthyl)-
hydroxymethyl] 2-naphthalene carboxylic acid Compound of formula III wherein
$R_1=R_2=R_3=R_4=$ —$CH_3$, R'—OH, R"—H and
R=$CO_2H$ To a solution of 0.7 g (1.8 mmoles) of 6-[(5,5,8,8-tetramethyl-5,6,7,8-tetrahydro-2-naphthyl)carbonyl] 2-naphthalene carboxylic acid, obtained in Example VII, in 25 cm³ of anhydrous tetrahydrofuran, there are added, in portions, over about a 10 minute period, 170 mg (4.5 mmoles) of sodium borohydride. The reaction mixture is stirred for 20 hours at ambient temperature. Once the reduction is completed, the reaction mixture is cooled to a temperature between 0° and 5° C. and then acidified by the slow addition of 0.1N HCl. After extraction with ethyl ether, the ether phase is washed with water, dried on sodium sulfate and evaporated to dryness. The resulting solid is recystallized in a toluene/hexane mixture. After drying, 0.6 g of white crystals of 6-[(5,5,8,8-tetramethyl-5,6,7,8-tetrahydro-2-naphthyl)-hydroxymethyl] 2-naphthalene carboxylic acid, having a melting point of 216°-8° C., is obtained.

NMR ¹H spectrum 250 MHz confirms to the expected structure.

Elemental analysis: $C_{26}H_{28}O_3$: Calculated: C 80.38, H 7.26, O 12.36. Found: C 80.53, H 7.28, O 12.31.

EXAMPLE X

Preparation of N-ethyl
6-[(5,5,8,8-tetramethyl-5,6,7,8-tetrahydro-2-naphthyl)-
hydroxymethyl] 2-naphthalene carboxamide Compound of formula III wherein
$R_1=R_2=R_3=R_4=$ —$CH_3$ R'=OH, R"=H and
R= —$CONHC_2H_5$ To a solution of 0.85 g (2 mmoles) of N-ethyl 6-[(5,5,8,8-tetramethyl-5,6,7,8-tetrahydro-2-naphthyl)carbonyl] 2-naphthalene carboxamide, obtained in Example VIII, in 25 cm³ of anhydrous tetrahydrofuran, there are added 300 mg (8 mmoles) of sodium borohydride. The reaction mixture is stirred for 72 hours at ambient temperature. The reaction mixture is then cooled to a temperature between 0° and 5° C., acidified by the slow addition of 0.1N HCl and then extracted with ethyl ether. The ether phase is washed with water, dried on sodium sulfate and evaporated to dryness. The resulting white solid is recrystallized in an isopropylether/acetone mixture. After drying, 0.7 g of white needles of N-ethyl 6-[(5,5,8,8-tetramethyl-5,6,7,8-tetrahydro-2-naphthyl)hydroxymethyl] 2-naphthalene carboxamide, having a melting point of 175° C., is obtained.

NMR ¹H spectrum 80 MHz conforms to the expected structure.

Elemental analysis: $C_{28}H_{33}NO_2$: Calculated: C 80.92, H 8.00, N 3.37, O 7.70. Found: C 81.00, H 8.11, N 3.53, O 7.88.

EXAMPLE XI

Preparation of
1-(5,5,8,8-tetramethyl-5,6,7,8-tetrahydro-2-naphthyl)-
-(6-carboxy-2-naphthyl)methane Compound of formula III wherein
$R_1=R_2=R_3=R_4=$—$CH_3$, $R'=R''=$H and $R=CO_2H$ To a suspension of 2 g (0.03 mole) of powdered zinc in $cm^3$ of glacial acetic acid, there is added 1 g (2.6 mmoles) of 6-[(5,5,8,8-tetramethyl-5,6,7,8-tetrahydro-2-naphthyl)carbonyl] 2-naphthalene carboxylic acid obtained in Example VII. The reaction mixture is then heated for 1 hour at reflux, at which point 2 $cm^3$ of 12N HCl are added and reflux is maintained for 45 minutes. After cooling to ambient temperature and adding 20 $cm^3$ of 12N HCl, the reaction mixture is diluted with 100 $cm^3$ of water and extracted with dichloromethane. The organic phase is washed with water, dried on sodium sulfate and concentrated under reduced pressure. The resulting crude product is recrystallized in a hexane/acetone mixture. 0.7 g of white crystals of 1-(5,5,8,8-tetramethyl-5,6,7,8-tetrahydro-2-naphthyl)-1 (6-carboxy-2-naphthyl) methane, having a melting point of 212° C., is obtained.

NMR $^1$H spectrum 80 MHz conforms to the expected structure.

Elemental analysis: $C_{26}H_{28}O_2$: Calculated: C 83.83, H 7.58, O 8.59. Found: C 83.63, H 7.63, O 8.73.

EXAMPLE XII

Preparation of
6-[(5,5,8,8-tetramethyl-5,6,7,8-tetrahydro-2-naphthyl)acetoxymethyl] 2-naphthalene carboxylic acid Compound of formula III wherein
$R_1=R_2=R_3=R_4=$—$CH_3$, $R'$—$OCOCH_3$, $R''=$H and $R=$—$CO_2H$ A solution of 0.5 g (1.29 mmoles) of 6-[(5,5,8,8-tetramethyl-5,6,7,8-tetrahydro-2-naphthyl)hydroxymethyl] 2-naphthalene carboxylic acid, obtained in Example IX, in 50 $cm^3$ of anhydrous dichloromethane and 3.5 $cm^3$ (31 mmoles) of acetic anhydride is stirred for one week at ambient temperature. The reaction mixture is then poured into 50 $cm^3$ of water and the dichloromethane phase is decanted, washed abundantly with water, dried on sodium sulfate and concentrated under reduced pressure. The resulting oil is purified by chromatography on silica 60 in the eluant mixture of acetic acid/dioxane/toluene, 2/8/90, respectively. After evaporation and drying, the resulting white solid is recrystallized in hexane containing a trace of acetone. 0.33 g of white crystals of 6-[(5,5,8,8-tetramethyl-5,6,7,8-tetrahydro-2-naphthyl)acetoxymethyl] 2-naphthalene carboxylic acid, having a melting point of 178° C., is obtained.

NMR $^1$H spectrum 80 MHz conforms to the expected structure.

Elemental analysis: $C_{28}H_{30}O_4$: Calculated: C 78.11, H 7.02, O 14.87. Found: C 78.08, H 7.07, O 14.66.

EXAMPLE XIII

Preparation of
6-[2-(5,5,8,8-tetramethyl-5,6,7,8-tetrahydro-2-naphthyl)-2-ethenyl] 2-methyl naphthalene carboxylate Compound of formula III wherein
$R_1=R_2=R_3=R_4=$—$CH_3$, $R'$ and $R''=$methano and $R=$—$CO_2CH_3$ To a solution of 20 $cm^3$ of anhydrous tetrahydrofuran, stirred at ambient temperature, there are added 1.3 g (3.1 mmole) of an equimolar mixture of triphenylmethyl phosphonium bromide and sodium amide and then after a 10 minute period, 1.2 g (3 mmoles) of 6-[(5,5,8,8-tetramehtyl-5,6,7,8-tetrahydro-2-naphthyl)carbonyl] 2-methylnaphthalene carboxylate, obtained in accordance with Example VI. The reaction is complete after 6 hours of stirring at ambient temperature. After adding 100 $cm^3$ of toluene and then 50 g of silica 60, the reaction mixture is filtered on "Celite" and the filtrate is concentrated under reduced pressure. The resulting solid is purified by chromatography on silica gel 60 by elution with dichloromethane, followed by recrystallization in methanol. After drying, 0.9 g of white needles of 6-[2-(5,5,8,8-tetramethyl-5,6,7,8-tetrahydro-2-naphthyl)-2-ethenyl] 2-methyl naphthalene carboxylate, having a melting point of 135° C., is obtained.

NMR $^1$H spectrum 250 MHz conforms to the expected structure.

Elemental analysis: $C_{28}H_{30}O_2$: Calculated: C 84.38, H 7.59, O 8.03. Found: C 84.28, H 7.54, O 8.12.

EXAMPLE XIV

Preparation of
6-[2-(5,5,8,8-tetramethyl-5,6,7,8-tetrahydro-2-naphthyl)-2-ethenyl] 2-naphthalene carboxylic acid Compound of formula III wherein
$R_1=R_2=R_3=R_4=$—$CH_3$, $R'$ and $R''$-methano and $R=$—$CO_2H$ A suspension of 0.75 g of 6-[2-(5,5,8,8-tetramethyl-5,6,7,8-tetrahydro-2-naphthyl)-2-ethenyl] 2-methyl naphthalene carboxylate, obtained in Example XIII, is stirred for 1 hour in a mixture of 15 $cm^3$ of ethyl alcohol and 15 $cm^3$ of 6N aqueous potash heated at reflux. After adding 100 $cm^3$ of water, the alcohol is removed by evaporation under a vacuum. The insoluble carboxylate is recovered and taken up in a mixture of 100 $cm^3$ of tetrahydrofuran and 50 $cm^3$ of water. After cooling to a temperature between 0° and 5° C., the reaction mixture is acidified by adding 1N HCl and then extracted with ether. The organic phase is washed with water, dried on sodium sulfate and then concentrated under reduced pressure. The resulting white solid is recrystallized in a heptane/acetone mixture. After drying, 0.6 g of white needles of 6-[2-(5,5,8,8-tetramethyl-5,6,7,8-tetrahydro-2-naphthyl)-2-ethenyl] 2-naphthalene carboxylic acid, having a melting point of 220° C., is obtained.

NMR $^1$H spectrum 250 MHz conforms to the expected structure.

Elemental analysis: $C_{27}H_{28}O_2$: Calculated: C 84.34, H 7.34, O 8.32. Found: C 84.20, H 7.30, O 8.40.

EXAMPLES XV AND XVI

Preparation of
6-[(5,5,8,8-tetramethyl-5,6,7,8-tetrahydro-2-naphthyl)-hydroxymethyl] 2-naphthalene carbinol Compound of formula III wherein
$R_1=R_2=R_3=R_4=-CH_3$, $R'=OH$, $R''=H$ and $R=CH_2OH$ and of 6-[(5,5,8,8-tetramethyl-5,6,7,8-tetrahydro-2-naphthyl)-butoxymethyl] 2-naphthalene carbinol Compound of formula III wherein
$R_1=R_2=R_3=R_4=-CH_3$, $R'=-OC_4H_9$, $R''=H$ and $R=-CH_2OH$ To a solution of 1.55 g (4 mmoles) of 6-[(5,5,8,8-tetramethyl-5,6,6,8-tetrahydro-2-naphthyl)carbonyl] 2-naphthalene carboxylic acid, obtained in accordance with Example VII, in 5 cm³ of anhydrous tetrahydrofuran, cooled to a temperature of −30° C. and maintained under argon, there are added 40 cm³ of a molar solution of borane in tetrahydrofuran. The reaction mixture is stirred for 2 hours while permitting it to return to ambient temperature. The solution is then left overnight at ambient temperature at which point it is cooled to a temperature of about 0° C., acidified by slowly adding 60 cm³ of 1N HCl and extracted with ethyl ether. The organic phase is washed with water, dried on sodium sulfate and then concentrated under reduced pressure. The resulting crude oil contains two products which are separated by chromatography on silica gel 60 in the eluant mixture of acetic acid/dioxane/toluene, 2/8/90 respectively. Each of these products is again purified separately by chromatography on silica in the same eluant mixture. There are thus obtained 0.6 g of 6-[(5,5,8,8-tetramethyl-5,6,7,8-tetrahydro-2-naphthyl)hydroxymethyl] 2-naphthalene carbinol in the form of a white powder having a melting point of 157° C. and 0.8 g of a colorless thick oil corresponding to 6-[(5,5,8,8-tetramethyl-5,6,7,8-tetrahydro-2-naphthyl)butoxymethyl] 2-naphthalene carbinol.

The NMR ¹H spectra 250 MHz of the two compounds conform to the described structure.

Elemental analyses, respectively:
(1) $C_{26}H_{30}O_2$: Calculated: C 83.38, H 8.07, O 8.55. Found: C 83.43, H 8.08, O 8.59.
(2) $C_{28}H_{34}O_2$: Calculated: C 83.54, H 8.51, O 7.95. Found: C 83.54, H 8.72, O 8.18.

EXAMPLE XVII

Preparation of
6-[(5,5,8,8-tetramethyl-5,6,7,8-tetrahydro-2-naphthyl)-butoxymethyl] 2-naphthalene carboxylic acid Compound of formula III wherein
$R_1=R_2=R_3=R_4=-CH_3$, $R'=-OC_4H_9$, $R''=H$ and $R=-CO_2H$

First Method

To a solution of 0.6 g (1.5 mmoles) of 6-[(5,5,8,8-tetramethyl-5,6,7,8-tetrahydro-2-naphthyl)hydroxymethyl] 2-naphthalene carboxylic acid, obtained in Example IX, in 20 cm³ of tetrahydrofuran and stirred at ambient temperature, there are added 10 cm³ of 12N HCl and then 2 g of anhydrous calcium chloride.

After stirring for 1 hour, 75 cm³ of ethyl ether are added and the aqueous phase is decanted. The organic phase is washed with water, dried on sodium sulfate and evaporated to dryness. 0.62 g of crude 6-[(5,5,8,8-tetramethyl-5,6,7,8-tetrahydro-2-naphthyl)chloromethyl] 2-naphthalene carboxylic acid (white solid) is obtained. There are then added 20 cm³ of primary butyl alcohol and the reaction mixture is stirred for 30 minutes at 60° C. and then concentrated under reduced pressure. The resulting oil is purified by chromatography on silica gel 60 in the eluant mixture of acetic acid/dioxane/toluene, 2/8/90 respectively. After evaporation and drying under a vacuum at 80° C., 0.54 g of 6-[(5,5,8,8-tetramethyl-5,6,7,8-tetrahydro-2-naphthyl)butoxymethyl] 2-naphthalene carboxylic acid in the form of a white powder, having a melting point of 71°-73° C., is obtained.

NMR ¹H spectrum 80 MHz conforms to the expected structure.

Elemental analysis: $C_{30}H_{36}O_3$: Calculated: C 81.04, H 8.16, O 10.80. Found: C 80.64, H 8.21, O 11.20.

Second Method

To a solution of 0.4 g (1 mmole) of 6-[(5,5,8,8-tetramethyl-5,6,7,8-tetrahydro-2-naphthyl)butoxymethyl] 2-naphthalene carbinol, obtained in accordance with Example XVI, in 10 cm³ of acetone and stirred at ambient temperature, there is added a solution of 0.3 g of chrome anhydride in 1.5 cm³ of water and 0.25 cm³ of 98% $H_2SO_4$.

After stirring for 5 hours at ambient temperature, the reaction mixture is diluted with 25 cm³ of water and extracted three times with 100 cm³ of ethyl ether. The ether phase is washed with water, dried on sodium sulfate and evaporated to dryness. The resulting crude solid is purified by chromatography on silica gel 60 in the eluant mixture, acetic acid/dioxane/toluene, 2/8/90 respectively. After evaporation and drying, 0.26 g of 6-[(5,5,8,8-tetramethyl-5,6,7,8-tetrahydro-2-naphthyl)-butoxymethyl] 2-naphthalene carboxylic acid, in the form of a white solid having a melting point of 72°-73° C., is obtained.

NMR ¹H spectrum 80 MHz conforms to the expected structure.

EXAMPLE XVIII

Preparation of
6-[(5,5,8,8-tetramethyl-5,6,7,8-tetrahydro-2-naphthyl) hydroxymethyl] 2-naphthaldehyde compound of formula III wherein $R_1=R_2=R_3=R_4=-CH_3$, $R'=OH$, $R''=H$ and $R=-CH=O$ To a solution of 1.4 g (3.7 mmoles) of 6-[(5,5,8,8-tetramethyl-5,6,7,8-tetrahydro-2-naphthyl) hydroxymethyl] 2-naphthalene carbinol, obtained in accordance with Example XV, in 25 cm³ of anhydrous dichloromethane, there is added, in portions, over a 10 minute period, 0.8 g (3.7 mmoles) of pyridinium chlorochromate. The reaction mixture is stirred for 1 hour at ambient temperature and then filtered on "Celite". The filtrate is concentrated under reduced pressure and the resulting crude product is purified by chromatography on silica gel 60 in dichloromethane, followed by recrystallization in hexane containing a little acetone.

After filtration and drying, 0.7 g of white needles of 6-[(5,5,8,8-tetramethyl-5,6,7,8-tetrahydro-2-naphthyl)-hydroxymethyl] 2-naphthaldehyde, having a melting point of 148° C., is obtained.

NMR ¹H spectrum 250 MHz conforms to the expected structure.

Elemental analysis: $C_{26}H_{28}O_2$: Calculated: C 83.83, H 7.58, O 8.59. Found: C 84.17, H 7.37, O 8.43.

EXAMPLE XIX

Preparation of 6-[(5,5,8,8-tetramethyl-5,6,7,8-tetrahydro-2-naphthyl) hydroxyiminomethyl] 2-ethyl naphthalene carboxylate.

Compound of formula III wherein
$R_1=R_2=R_3=R_4=-CH_3$, R' and R"=hydroxyimino and R=$-CO_2C_2H_5$ A suspension of 1.94 g (5 mmoles) of 6-[(5,5,8,8-tetramethyl-5,6,7,8-tetrahydro-2-naphthyl)carbonyl] 2-naphthalene carboxylic acid in 100 cm³ of absolute ethanol containing 0.2 cm³ of 98% $H_2SO_4$ is heated at reflux until complete transformation into the ethyl ester (16 hours).

There are then added 695 mg (10 mmoles) of hydroxylamine hydrochloride and then 1.9 cm³ (13.5 mmoles) of triethylamine. The reaction mixture is again heated for 15 hours at reflux. The solution is cooled to ambient temperature and concentrated under reduced pressure. The residue is taken up in a 50/50 tetrahydrofuran-/ethyl ether mixture, washed with 0.1N HCl and then with water. The resulting solution is dried on sodium sulfate and evaporated to dryness. The white solid thus isolated is rapidly purified by chromatography on silica gel 60 in dichloromethane, followed by recrystallization in a minimum of boiling ethanol. After drying, 1.9 g of white needles of 6-[(5,5,8,8-tetramethyl-5,6,7,8-tetrahydro-2-naphthyl) hydroxyiminomethyl] 2-ethyl naphthalene carboxylate, having a melting point of 179°–180° C., are obtained.

NMR ¹H spectrum 80 MHz conforms to the expected structure.

Elemental analysis: $C_{28}N_{31}NO_3$: Calculated: C 78.29, H 7.27, N 3.26, O 11.17. Found: C 78.31, H 7.23, N 3.39, O 11.41.

EXAMPLE XX

Preparation of 6-[(5,5,8,8-tetramethyl-5,6,7,8-tetrahydro-2-naphthyl) hydroxyiminomethyl] 2-naphthalene carboxylic acid Compound of formula III wherein
$R_1=R_2=R_3=R_4=-CH_3$, R' and R"=hydroxyimino and R=$-COOH$ A solution of 0.76 g (1.8 mmoles) of 6-[(5,5,8,8-tetramethyl-5,6,7,8-tetrahydro-2-naphthyl) hydroxyiminomethyl] 2-ethyl naphthalene carboxylate, obtained in accordance with Example XIX, in 10 cm³ of absolute alcohol and 10 cm³ of 2N aqueous potash is heated for 2 hours at 50°–60° C. After adding 100 cm³ of water, the alcohol is evaporated under reduced pressure. The resulting aqueous solution is cooled to a temperature between 0° and 5° C. and then acidified with 5 cm³ of 12N HCl. The resulting precipitate is filtered, washed with water, dried under a vacuum on potash at 70°–80° C. and then recrystallized in a hexane/acetone mixture. After drying, 0.65 g of white crystals of 6-[(5,5,8,8-tetramethyl-5,6,7,8-tetrahydro-2-naphthyl) hydroxyiminomethyl] 2-naphthalene carboxylic acid, having a melting point of 247° C., is obtained.

The NMR ¹H 250 MHz and IR spectra conform to the expected structure.

EXAMPLE XXI

Preparation of N-ethyl 6-[(5,5,8,8-tetramethyl-5,6,7,8-tetrahydro-2-naphthyl) hydroxyiminomethyl] 2-naphthalene carboxamide Compound of formula III wherein
$R_1=R_2=R_3=R_4=-CH_3$, R' and R"=hydroxyimino and R=$-CONHC_2H_5$ To a suspension of 1.24 g (3 mmoles) of N-ethyl 6-[(5,5,8,8-tetramethyl-5,6,7,8-tetrahydro-2-naphthyl) carbonyl] 2-naphthalene carboxamide and 695 mg (10 mmoles) of hydroxylamine hydrochloride in 40 cm³ of of absolute alcohol, there are added 1.06 g (10 mmoles) of sodium carbonate. The reaction mixture is heated for 24 hours at reflux. The solution is then evaporated to dryness and the residue is taken up in 100 cm³ of dichloromethane. After washing with water, the dichloromethane phase is dried on sodium sulfate and concentrated under reduced pressure. The resulting pale yellow solid is purified by chromatography on silica gel 60, eluted with a toluene/dichloromethane/ethyl acetate mixture, 5/3/2, respectively, followed by recrystallization in toluene. 0.9 g of white crystals of N-ethyl 6-[(5,5,8,8-tetramethyl-5,6,7,8-tetrahydro-2-naphthyl) hydroxyiminomethyl] 2-naphthalene carboxamide, having a melting point of 189° C., is obtained.

NMR ¹H 250 MHz and IR spectra conform to the expected structure.

Elemental analysis: $C_{28}H_{32}N_2O_2$: Calculated: C 78.47, H 7.53, N 6.54, O 7.47. Found: C 77.99, H 7.56, N 6.53, O 7.85.

EXAMPLE XXII

Preparation of 6-[(5,5,8,8-tetramethyl-5,6,7,8-tetrahydro-2-naphthyl-)amino methyl] 2-ethyl naphthalene carboxylate Compound of formula III wherein
$R_1=R_2=R_3=R_4=-CH_3$, R'=$NH_2$, R"=H and R=$-CO_2C_2H_5$ To a suspension of 1.5 g (0.023 mole) of powdered zinc in 20 cm³ of glacial acetic acid, there is added 0.9 g (2.1 mmoles) of 6-[(5,5,8,8-tetramethyl-5,6,7,8-tetrahydro-2-naphthyl) hydroxyiminomethyl] 2-ethyl naphthalene carboxylate, obtained in Example XIX. The reaction mixture is heated for 30 minutes at 80° C. After cooling to ambient temperature, there are added 100 cm³ of dichloromethane and the reaction mixture is filtered. The filtrate is washed three times with 50 cm³ of a 5% aqueous ammonia solution, then with water, dried on sodium sulfate and evaporated to dryness. The resulting white solid is recrystallized in hexane. After drying, 0.69 g of white needles of 6-[(5,5,8,8-tetramethyl-5,6,7,8-tetrahydro-2-naphthyl) aminomethyl] 2-ethyl naphthalene carboxylate, having a melting point of 126° C., is obtained.

NMR ¹H spectrum 80 MHz conforms to the expected structure.

Elemental analysis: $C_{28}H_{33}NO_2$: Calculated: C 80.92, H 8.00, N 3.37, O 7.70. Found: C 80.74, H 8.03, N 3.42, O 7.97.

EXAMPLE XXIII

Preparation of
6-[(5,5,8,8-tetramethyl-5,6,7,8-tetrahydro-2-naphthyl) amino methyl] 2-naphthalene carboxylic acid Compound of formula III wherein
$R_1=R_2=R_3=R_4=$—$CH_3$, R'=$NH_2$, R''=H and
R=—$CO_2H$ A solution of 0.63 g (1.51 mmoles) of 6-[(5,5,8,8-tetramethyl-5,6,7,8-tetrahydro-2-naphthyl) aminomethyl] 2-ethyl naphthalene carboxylate, obtained in Example XXII, in 10 cm$^3$ of absolute alcohol and 10 cm$^3$ of 2N aqueous potash is heated for 2 hours at 60°–70° C. After adding 100 cm$^3$ of water, the alcohol is evaporated under reduced pressure. The resulting aqueous solution is cooled to a temperature between 0° and 5° C. and then acidified by adding 12N HCl. The resulting precipitate is filtered, washed with water, dried under a vacuum at 80° C. on potash and then washed with ethylether. After drying, 0.54 g of 6-[(5,5,8,8-tetramethyl-5,6,7,8-tetrahydro-2-naphthyl) aminomethyl] 2-naphthalene carboxylic acid, in the form of a white powder having a melting point of 286°–288° C., is obtained.

NMR $^1$H 250 MHz and IR spectra conform to the expected structure.

EXAMPLE XXIV

Preparation of
6-[(5,8-methano-5,6,7,8-tetrahydro-2-naphthyl) carbonyl] 2-methyl naphthalene carboxylate Compound of formula IV wherein R' and R''=oxo and
R=—$CO_2CH_3$ To a suspension of 1.08 g (7.5 mmoles) of 1,4-methano-1,2,3,4-tetrahydro naphthalene and 2 g (8 mmoles) of 6-methoxycarbonyl-2-naphthalene carboxylic acid chloride in 30 cm$^3$ of anhydrous 1,2-dichloroethane, there are added, in portions, over a 45 minute period, 1.3 g (9.75 mmoles) of anhydrous aluminum chloride. The mixture is stirred for 5 hours at ambient temperature and then poured into 80 cm$^3$ of acidulated ice water. The organic phase is decanted. The aqueous phase is once again extracted with 60 cm$^3$ of 1,2-dichloroethane. The 1,2-dichloroethane phases are combined, washed with sodium bicarbonate, dried on sodium sulfate and then concentrated. The resulting solid is dried under a vacuum at 60° C., then recrystallized initially in ethyl acetate, and finally in isopropanol. 1 g of 6-[(5,8-methano-5,6,7,8-tetrahydro-2-naphthyl) carbonyl] 2-methyl naphthalene carboxylate, in the form of white crystals having a melting point of 119° C., is obtained.

NMR $^1$H spectrum 60 MHz conforms to the expected structure.

Elemental Analysis: $C_{24}H_{20}O_3$: Calculated: C 80.87, H 5.66, O 13.47. Found: C 80.82, H 5.69, O 13.25.

EXAMPLE XXV

Preparation of
6-[(5,8-methano-5,6,7,8-tetrahydro-2-naphthyl) carbonyl] 2-naphthalene carboxylic acid Compound of formula IV wherein R' and R''=oxo and
R=—$CO_2H$ A suspension of 0.88 g (2.46 mmoles) of 6-[(5,8-methano-5,6,7,8-tetrahydro-2-naphthyl) carbonyl] 2-methyl naphthalene carboxylate, obtained in Example XXIV, is stirred for 2 hours in a mixture of 15 cm$^3$ of alcohol and 15 cm$^3$ of 6N aqueous potash heated at reflux. After having added 60 cm$^3$ of water, the alcohol is removed by evaporation under a vacuum. The resulting aqueous phase is cooled to a temperature between 0° and 5° C. and then acidified by adding 15 cm$^3$ of 12N HCl. The resulting precipitate is filtered, washed with water and dried at 80° C. on potash.

After recrystallization in 110 cm$^3$ of methanol, 0.62 g of white crystals of 6-[(5,8-methano-5,6,7,8-tetrahydro-2-naphthyl) carbonyl] 2-naphthalene carboxylic acid, having a melting point of 243° C. is obtained.

NMR $^1$H 250 MHz and $^{13}$C spectra conform to the expected structure.

Elemental analysis: $C_{23}H_{18}O_3$: Calculated: C 80.68, H 5.30, O 14.02. Found: C 80.83, H 5.43, O 13.71.

EXAMPLE XXVI

Preparation of 6-[(5,6,7,8-tetrahydro-2-naphthyl) carbonyl] 2-methyl naphthalene carboxylate Compound of formula III wherein
$R_1=R_2=R_3=R_4=$H, R' and R''=oxo and
R=—$CO_2CH_3$ To a suspension of 1.59 g (12 mmoles) of 1,2,3,4-tetrahydro naphthalene and 3 g (12.05 mmoles) of 6-methoxy carbonyl-2-naphthalene carboxylic acid in 60 cm$^3$ of anhydrous 1,2-dichloroethane, there are added in portions 2.4 g (18 mmoles) of anhydrous aluminum chloride. The mixture is stirred for 6 hours at ambient temperature and then poured into 100 cm$^3$ of acidulated ice water. The organic phase is decanted. The aqueous phase is extracted once again with 100 cm$^3$ of 1,2-dichloroethane. The dichloroethane phases are combined, washed with sodium bicarbonate, dried on sodium sulfate and then concentrated to dryness. The resulting crude ester is rapidly purified by chromatography on silica gel with an 8/2 hexane/ether mixture and then recrystallized in isopropanol. 2 g of white crystals of 6-[(5,6,7,8-tetrahydro-2-naphthyl) carbonyl] 2-methyl naphthalene carboxylate, having a melting point of 171° C., are obtained.

NMR $^1$H spectrum conforms to the expected structure.

Elemental analysis: $C_{23}H_{20}O_3$: Calculated: C 80.21, H 5.85, O 13.94. Found: C 80.16, H 5.91, O 13.85.

EXAMPLE XXVII

Preparation of 6-[(5,6,7,8-tetrahydro-2-naphthyl) carbonyl] 2-naphthalene carboxylic acid Compound of formula III wherein
$R_1=R_2=R_3=R_4=$H, R' and R''=oxo and
R=—COOH A suspension of 1.50 g (4.35 mmoles) of 6-[(5,6,7,8-tetrahydro-2-naphthyl) carbonyl] 2-methyl naphthalene carboxylate, obtained in Example XXVI, is stirred for 3 hours in a mixture of 25 cm$^3$ of alcohol and 25 cm$^3$ of 6N aqueous potash heated at reflux. After having added 50 cm$^3$ of water, the alcohol is removed by evaporation under a vacuum. The resulting aqueous phase is diluted to 500 cm$^3$ to completely solubilize the carboxylate and then acidified by adding 25 cm$^3$ of 12N HCl. The resulting precipitate is filtered, washed with water and dried at 80° C. on potash.

After recrystallization initially in isopropanol and then in an 8/2 methanol/acetone mixture, 1.1 g of white crystals of 6-[(5,6,7,8-tetrahydro-2-naphthyl) carbonyl]

2-naphthalene carboxylic acid, having a melting point of 267° C. are obtained.

NMR $^1$H 250 MHz and $^{13}$C spectra conform to the expected structure.

Elemental analysis: $C_{22}H_{18}O_3$: Calculated: C 79.98, H 5.49, O 14.53. Found: C 80.18, H 5.52, O 14.24.

EXAMPLE XXVIII

Preparation of N-ethyl 6-[(5,6,7,8-tetrahydro-2-naphthyl) carbonyl] 2-naphthalene carboxamide Compound of formula III wherein
$R_1=R_2=R_3=R_4=H$, R' and R''=oxo and
R=—CONHC$_2$H$_5$ A suspension of 165 g (0.5 mmole) of 6-[(5,6,7,8-tetrahydro-2-naphthyl) carbonyl] 2-naphthalene carboxylic acid, obtained in Example XXVII, and 97.5 mg (0.6 mmole) of N,N'-carbonyldiimidazole in 5 cm$^3$ of dry dichloromethane is stirred for 2 hours at ambient temperature. There is then added 0.04 cm$^3$ (0.6 mmoles) of anhydrous ethylamine to the resulting solution. After stirring for 30 minutes, the reaction mixture is diluted with 10 cm$^3$ of water, washed successively with 10 cm$^3$ of normal soda, twice with 10 cm$^3$ of water, with 10 cm$^3$ of 1N HCl, and with 10 cm$^3$ of water. The dichloromethane phase is dried on sodium sulfate and evaporated by dryness. The crude amide is dried under a vacuum at 60° C., then recrystallized in isopropyl ether containing a little methanol. 130 mg of pale yellow needles of N-ethyl 6-[(5,6,7,8-tetrahydro-2-naphthyl) carbonyl] 2-naphthalene carboxylate, having a melting point of 137° C., are obtained.

NMR $^1$H 250 MHz and $^{13}$C spectra conform to the expected structure.

Elemental analysis: $C_{24}H_{23}NO_2$: Calculated: C 80.64, H 6.49, N 3.92, O 8.95. Found: C 80.49, H 6.55, N 3.86, O 8.75.

EXAMPLE XXIX

Preparation of 6-[(5,5,8,8-tetramethyl-5,6,7,8-tetrahydro-2-naphthyl) carbonyl] 2-naphthalene carboxaldehyde Compound of formula III wherein
$R_1=R_2=R_3=R_4=CH_3$, R' and R''=oxo and
R=—CH=O This compound is prepared in two stages starting with 6-[(5,5,8,8-tetramethyl-5,6,7,8-tetrahydro-2-naphthyl) carbonyl] 2-naphthalene carboxylic acid prepared in Example VII. In the first stage the carbonyl and the carboxylic acid functions are reduced in alcohol. In the second stage the 6-[(5,5,8,8-tetramethyl-5,6,7,8-tetrahydro-2-naphthyl) hydroxymethyl] 2-naphthalene carbinol is oxidized to the expected aldehyde.

(a) Preparation of 6-[(5,5,8,8-tetramethyl-5,6,7,8-tetrahydro-2-naphthyl) hydroxymethyl] 2-naphthalene carbinol To a suspension of 225 mg (6 mmoles) of lithium aluminum hydride in 10 cm$^3$ of anhydrous tetrahydrofuran stirred at 0° C., there are added, all at once, 1.16 g (3 mmoles) of the acid prepared in accordance with Example II. After one hour, the reaction mixture is stirred at ambient temperature, the reaction being monitored by C.C.M. When all of the initial reactant is transformed 100 cm$^3$ of 0.1N HCl are slowly added. The mixture is then extracted 4 times with 25 cm$^3$ of ethyl ether. The ether phases are decanted, dried on sodium sulfate and the solvent is removed by evaporation under a vacuum.

The resulting crude diol is purified by passage through a silica gel column and eluted with a acetic acid/dioxane/toluene mixture, 2/8/90 respectively.

After evaporation of the eluant 0.9 g of 6-[(5,5,8,8-tetramethyl-5,6,7,8-tetrahydro-2-naphthyl) hydroxymethyl] 2-naphthalene carbinol, in the form of white crystals having a melting point of 157° C., is obtained.

NMR $^1$H 60 MHz spectrum conforms to the expected structure.

(b) Oxidation of the preceding diol

To a solution of 0.8 g (2.1 mmoles) of the diol prepared above in part (a) in 20 cm$^3$ of anhydrous dichloromethane, stirred at ambient temperature, there is added 0.55 g (2.5 mmoles) of pyridinium chlorochromate. After 45 minutes 30 g of silica gel are added and the whole is filtered on "Celite". The filter is washed with dichloromethane and the solution is concentrated under reduced pressure. The resulting product is purified by chromatography on silica gel and eluted with an acetic acid/dioxane/toluene mixture, 2/8/90 respectively. After concentrating the elution phases, then recrystallization in hexane, 0.52 g of 6-[(5,5,8,8-tetramethyl-5,6,7,8-tetrahydro-2-naphthyl) carbonyl] 2-naphthalene carboxaldehyde, in the form of white crystals having a melting point of 131° C., is obtained NMR $^1$H spectrum 250 MHz conforms to the expected structure.

Elemental analysis: $C_{26}H_{26}O_2$: Calculated: C 84.29, H 7.07, O 8.64. Found: C 84.21, H 6.96, O 8.46.

EXAMPLE XXX

Preparation of 6-[(5,5,8,8-tetramethyl-5,6,7,8-tetrahydro-2-naphthyl) carbonyl] 2-naphthalene carbinol Compound of formula III wherein
$R_1=R_2=R_3=R_4=CH_3$, R' and R''=oxo and
R=CH$_2$OH To an 85% solution of 0.3 g of potash in 10 cm$^3$ of methanol, stirred at 60° C., there are added 0.6 g (1.6 mmoles) of 6-[(5,5,8,8-tetramethyl-5,6,7,8-tetrahydro-2-naphthyl) carbonyl] 2-formyl naphthalene and 0.16 cm$^3$ (1.9 mmoles) of a 37% aqueous formaldehyde solution. After stirring for 2 hours at 60°-70° C., the methanol is distilled off under normal pressure. There are then added 10 cm$^3$ of water to the hot residue which is cooled to ambient temperature. The resulting precipitate is extracted 4 times with 25 cm$^3$ of ethyl ether. The ether phases are washed with water, dried on sodium sulfate and evaporated to dryness under reduced pressure. The crude product is purified by chromatography on silica gel 60 in the eluant mixture of acetic acid/dioxane/toluene, 2/8/90, respectively, followed by recrystallization in a hexane/acetone mixture. After drying, 240 mg of white crystals of 6-[(5,5,8,8-tetramethyl-5,6,7,8-tetrahydro-2-naphthyl) carbonyl] 2-naphthalene carbinol, having a melting point of 117° C., are obtained.

NMR $^1$H spectrum 250 MHz corresponds to the expected structure.

Elemental analysis: $C_{26}H_{23}O_2$: Calculated: C 83.83, H 7.58, O 8.59. Found: C 83.77, H 7.55, O 8.75.

EXAMPLE XXXI

Preparation of N-2′-hydroxy-2-ethoxy ethyl 6-[(5,5,8,8-tetramethyl-5,6,7,8-tetrahydro-2-naphthyl) carbonyl] 2-naphthalene carboxamide Compound of formula III wherein
$R_1=R_2=R_3=R_4=CH_3$, R′ and R″=oxo and
$R=-CONH(CH_2)_2O-(CH_2)_2-OH$.

To a suspension of 0.9 g (2.33 mmoles) of 6-[(5,5,8,8-tetramethyl-5,6,7,8-tetrahydro-2-naphthyl) carbonyl] 2-naphthalene carboxylic acid in 9 cm³ of anhydrous dichloromethane, there are added 490 mg (3.03 mmoles) of N,N′-carboxyldiimidazole. After stirring for 1 hour at ambient temperature, 0.27 cm³ (2.57 mmoles) of N-2-hydroxyethoxy ethylamine is added to the resulting solution. The reaction mixture is stirred for 3 hours at ambient temperature, then diluted with 25 cm³ of dichloromethane and washed with water and dilute HCl. The dichloromethane phase is dried on sodium sulfate and then evaporated to dryness. The crude amide is purified by chromatography on silica gel 60 in the eluant mixture of 70/30 dichloromethane/tetrahydrofuran. After evaporation and drying, there is obtained 0.65 g of white crystals of N-2′-hydroxy-2-ethoxy ethyl 6-[(5,5,8,8-tetramethyl-5,6,7,8-tetrahydro-2-naphthyl) carbonyl] 2-naphthalene carboxamide which becomes vitreous at 80° C.

NMR ¹H spectrum 250 MHz conforms to the expected structure.

Elemental analysis: $C_{30}H_{35}NO_4$: Calculated: C 76.08, H 7.45, N 2.96, O 13.51. Found: C 76.04, H 7.52, N 3.00, O 13.62.

EXAMPLE XXXII

Preparation of N-p-hydroxy phenyl 6-[(5,5,8,8-tetramethyl-5,6,7,8-tetrahydro-2-naphthyl) carbonyl] 2-naphthalene carboxamide Compound of formula III wherein
$R_1=R_2=R_3=R_4=CH_3$, R′ and R″=oxo and
$R=-CONHC_6H_4\ p\ OH$ To a suspension of 0.9 g (2.33 mmoles) of 6-[(5,5,8,8-tetramethyl-5,6,7,8-tetrahydro-2-naphthyl) carbonyl] 2-naphthalene carboxylic acid, obtained in accordance with Example VII, in 9 cm³ of anhydrous dichloromethane, there are added 490 mg (3.03 mmoles) of N,N′-carbonyl diimidazole. After stirring for 1 hour at ambient temperature, 1 cm³ of pure N,N-dimethyl formamide and 0.31 g (2.8 mmoles) of p-amino phenol are added to the resulting solution. The reaction mixture is stirred overnight at ambient temperature. Since the initial acid reactant has not completely reacted, there are added 0.1 g of N,N′-carbonyldiimidazole, and 0.1 g of p-aminophenol. The reaction mixture is stirred for 2 hours at ambient temperature. The reaction mixture is then diluted with 50 cm³ of dichloromethane, washed with dilute HCl and then with water until neutral. The dichloromethane phase is dried on sodium sulfate and then concentrated under reduced pressure. The crude amide is purified by chromatography on silica gel 60 is a 5/3/2 mixture of toluene/dichloromethane/ethylacetate. On recrystallization in an isopropylether/acetone mixture 0.33 g of white crystals of N-p-hydroxyphenol 6-[(5,5,8,8-tetramethyl-5,6,7,8-tetrahydro-2-naphthyl) carbonyl] 2-naphthalene carboxamide having a melting point of 268°–9° C. is obtained.

NMR ¹H is spectrum conforms to the expected structure.

Elemental analysis: $C_{32}H_{31}NO_3$: Calculated: C 80.47, H 6.54, N 2.93. Found: C 80.55, H 6.27, N 2.89.

During the course of the chromatography on silica, a second product is also isolated which, on recyrstallization in an acetone/methanol mixture, provides 0.3 g of white crystals of N,O-bis[2(5,5,8,8f-tetramethyl-5,6,7,8-tetrahydro-naphthyl)-2,6-dicarbonyl naphthyl] 4-amino phenol having a melting point of 239°–240° C.

NMR ¹H spectrum conforms to the described structure.

Elemental analysis: $C_{58}H_{55}NO_5$: Calculated: C 82.33, H 6.55, N 1.66, O 9.45. Found: C 82.13, H 6.73, N 1.65, O 9.25.

This decondensed product is saponified by 6N potash in a hydroalcoholic medium for 5 hours at 50° C. After dilution with water, evaporation of the alcohol under reduced pressure, and acidification with concentrated HCl, an equimolar mixture of N-p-hydroxyphenyl 6-[(5,5,8,8-tetramethyl-5,6,7,8-tetrahydro-2-naphthyl) carbonyl] 2-naphthlene carboxamide and 6-[(5,5,8,8-tetramethyl-5,6,7,8-tetrahydro-2-naphthyl) carbonyl] 2-naphthalene carboxylic acid is obtained. On chromatography on silica 60 in a 5/3/2 mixture of toluene/dichloromethane/ethyl acetate, a second fraction of 0.11 g of N-p-hydroxyphenyl 6-[(5,5,8,8-tetramethyl-5,6,7,8-tetrahydro-2-naphthyl) carbonyl] 2-naphthalene carboxamide, having a melting point identical to that given above, is obtained.

EXAMPLE XXXIII

Preparation of N-(1-ethoxycarbonyl-3-methylthiopropyl) 6-[(5,5,8,8-tetramethyl-5,6,7,8-tetrahydro-2-naphthyl) carbonyl] 2-naphthalene carboxamide Compound of formula naphthalene carboxamide Compound of formula III wherein
$R_1=R_2=R_3=R_4=CH_3$, R′ and R″=oxo and R=

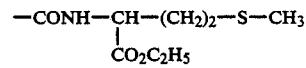

There is stirred for 1 hour and 30 minutes at 40°–50° C., a solution of 1.2 g (3.1 mmoles) of 6-[(5,5,8,8-tetramethyl-5,6,7,8-tetrahydro-2-naphthyl) carbonyl] 2-naphthalene carboxylic acid, obtained in Example VII, and 605 mg (3.72 mmoles) of N,N′-carbonyldiimidazole in 15 cm³ of anhydrous N,N-dimethyl formamide. The reaction mixture is cooled to 20° C. 730 mg (3.41 mmoles) of the hydrochloride of the ethyl ester of L-methionine and then 0.48 cm³ (3.41 mmoles) of triethylamine are added. After stirring initially for 1 hour at 20° C. and then for 2 hours at 40°–50° C., the reaction mixture is poured into 100 cm³ of aciduated water and stirred for 15 minutes. The resulting precipitate is filtered and abundantly washed with dilute HCl and then with water. After drying under a vacuum at 70° C. the precipitate is purified by chromatography on silica 60 in a 5/3/2 mixture of toluene/dichloromethane/ethyl acetate. After evaporation, there is obtained 0.8 g of N-(1-carbethoxy-3-methylthio propyl) 6-[(5,5,8,8-tetramethyl-5,6,7,8-tetrahydro-2-naphthyl) carbonyl] 2-naphthalene carboxamide in the form of a thick oil which is transformed into a vitreous product after prolonged drying under a vacuum at 70°–80° C.

NMR $^1$H spectrum 60 MHz corresponds to the expected structure.

EXAMPLE XXXIV

Prepration of N-(1-carboxy-3-methylthio propyl) 6-[(5,5,8,8-tetramethyl-5,6,7,8-tetrahydro-2-naphthyl) carbonyl] 2-naphthalene carboxamide Compound of formula III wherein $R_1=R_2=R_3=R_4=CH_3$, R' and R"=oxo and R=

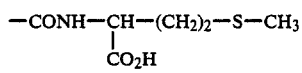

A suspension of 0.58 g (1 mmole) of N-(1-ethoxy carbonyl-3-methylthio propyl) 6-[(5,5,8,8-tetramethyl-5,6,7,8-tetrahydro-2-napthyl) carbonyl] 2-naphthalene carboxamide, obtained in Example XXXIII, is stirred for 30 minutes in a mixture of 5 cm$^3$ of alcohol and 5 cm$^3$ of 6N aqueous potash heated to 50° C. After adding 50 cm$^3$ of water, the alcohol is removed by evaporation under reduced prssure at 40°-45° C. The aqueous phase is then acidified with 3 cm$^3$ of 12N HCl. The resulting precipitate is filtered, thoroughly washed with water, dried on potash at 70° C. and then taken up in tepid isopropylether. After cooling, filtering and drying under a vacuum at 70° C., 0.4 of white crystals of N-(1-carboxy-3-methylthio propyl) 6-[(5,5,8,8-tetramethyl-5,6,7,8-tetrahydro-2-naphthyl) carbonyl] 2-naphthalene carboxamide, having a melting point of 171°-2° C., is obtained.

NMR $^1$H spectrum 250 MHz conforms to the expected structure.

Elemental analysis: $C_{31}H_{35}NO_4S.0.5H_2O$: Calculated: C 70.69, H 6.89, N 2.66, O 13.67, S 6.08. Found: C 70.95, H 6.87, N 2.59, O 13.55, S 5.98.

EXAMPLES OF COMPOSITIONS

A. Oral Compositions

EXAMPLE 1

0.2 g tablet

| | |
|---|---|
| 6-[(1,1,3,3-tetramethyl-5-indanyl) carbonyl] 2-naphthalene carboxylic acid | 0.005 g |
| Starch | 0.110 g |
| Dicalcium phosphate | 0.020 g |
| Silicon | 0.020 g |
| Lactose | 0.030 g |
| Talc | 0.010 g |
| Magnesium stearate | 0.005 g |

In this Example, the active compound can be replaced by the same amount of 6-[(1,1,2,3,3-pentamethyl-5-indanyl) carbonyl] 2-naphthalene carboxylic acid or 6-[(5,8-methano-5,6,7,8-tetrahydro-2-naphthyl) carbonyl] 2-napthalene carboxylic acid or even by 0.001 g of 6-[(5,5,8,8-tetramethyl-5,6,7,8-tetrahydro-2-naphthyl) carbonyl] 2-naphthalene carboxylic acid.

EXAMPLE 2

Drinkable Suspension in 5 ml Ampoules

| | |
|---|---|
| 6-[(1,1,2,3,3-pentamethyl-5-indanyl) hydroxymethyl] 2-naphthalene carboxylic acid | 0.005 g |
| Glycerine | 0.500 g |
| Sorbitol, 70% | 0.500 g |
| Sodium saccharinate | 0.010 g |
| Methyl parahydroxybenzoate | 0.040 g |
| Aroma, sufficient amount | |
| Purified water, sufficient amount for | 5.000 ml |

In this example, the active compound can be replaced by the same amount of 6-[(5,5,8,8-tetramethyl-5,6,7,8-tetrahydro-2-naphthyl) hydroxymethyl] 2-naphthalene carboxylic acid or by 0.001 g of N-ethyl 6-[(5,5,8,8-tetramethyl-5,6,7,8-tetrahydro-2-naphthyl) carbonyl] 2-naphthalene carboxamide.

B. Topical Compositions

EXAMPLE 3

Ointment

| | |
|---|---|
| N—ethyl 6-[(5,5,8,8-tetramethyl-5,6,7,8-tetrahydro-2-naphthyl) hydroxymethyl] 2-naphthalene carboxamide | 0.100 g |
| Isopropyl myristate | 81.620 g |
| Fluid petrolatum oil | 9.100 g |
| Silica, sold under the tradename "Aerosil 200" by Degussa | 9.180 g |

In this example the active compound can be replaced by 0.005 g of 6-[(1,1,3,3-tetramethyl-5-indanyl) carbonyl] 2-naphthalene carboxylic acid or even by 0.1 g of 6-[5,5,8,8-tetramethyl-5,6,7,8-tetrahydro-2-naphthyl) hydroxymethyl] 2-naphthalene carboxylic acid or by N-ethyl 6-[(5,5,8,8-tetramethyl-5,6,7,8-tetrahydro-2-naphthyl) carbonyl] 2-naphthalene carboxamide.

EXAMPLE 4

Anti-seborrhea cream

| | |
|---|---|
| Polyoxyethylenated stearate (40 moles of ethylene oxide) sold under the trade name "Myrij 52" by Atlas | 4.00 g |
| Mixture of the lauryl esters of sorbitol, polyoxyethylenated with 20 moles of ethylene oxide, sold under the trade name "Tween 20" by Atlas | 1.8 g |
| Mixture of mono- and distearate of glycerol, sold under the trade name "GELEOL" by Gattefosse | 4.2 g |
| Propylene glycol | 10.0 g |
| Butyl hydroxyanisole | 0.01 g |
| Butyl hydroxy toluene | 0.02 g |
| Cetyl-stearyl alcohol | 6.2 g |
| Preservative, sufficient amount | |
| Perhydrosqualene | 18 g |
| Mixture of caprylic-capric triglycerides sold under the trade name "Miglyol 812" by Dynamit Nobel | 4.0 g |
| S—carboxy methyl cysteine | 3.0 g |
| Triethanolamine, 99% | 2.5 g |
| N—ethyl 6-[(5,5,8,8-tetramethyl-5,6,7,8-tetrahydro-2-naphthyl) hydroxymethyl] 2-naphthalene carboxamide | 0.10 g |
| Water, sufficient amount for | 100 g |

EXAMPLE 5

Anti-sebarrhea cream

| | |
|---|---|
| Polyoxyethylenated stearate (40 moles ethylene oxide), sold under the trade name "Myrij 52" by Atlas | 4.0 g |
| Mixture of lauryl esters of sorbitol and sorbitan, polyoxyethylenated with 20 moles of ethylene oxide, sold under the trade name "Tween 20" by Atlas | 1.8 g |
| Mixture of mono- and distearate of glycerol, sold under the trade name "GELEOL" by Gattefosse | 4.2 g |
| Propylene glycol | 10.0 g |
| butyl hydroxy anisole | 0.01 g |
| Butyl hydroxy toluene | 0.02 g |
| Cetyl-stearyl alcohol | 6.2 g |
| Preservative, sufficient amount | |
| Perhydrosqualene | 18.0 g |
| Mixture of caprylic-capric triglycerides sold under the trade name "Miglyol 812" by Dynamit Nobel | 4.0 g |
| 5-amino-5-carboxy 3-thia pentanoate of 2-benzylthio ethyl ammonium | 3.0 g |
| 6-[(5,5,8,8-tetramethyl-5,6,7,8-tetrahydro-2-naphthyl) hydroxy methyl] 2-naphthalene carboxamide | 0.1 g |
| Water, sufficient amount for | 100 g |

EXAMPLE 6

Hair lotion

| | |
|---|---|
| Propylene glycol | 20.0 g |
| Ethanol | 34.87 g |
| Polyethylene glycol, molecular mass 400 | 40.0 g |
| Water | 4.0 g |
| Butyl hydroxy anisole | 0.01 g |
| Butyl hydroxy toluene | 0.02 g |
| N—ethyl 6-[(1,1,2,3,3-pentamethyl-2-indanyl) carbonyl] 2-naphthalene carboxamide | 0.10 g |
| Minoxidil | 1.0 g |

EXAMPLE 7

Anti-acne gel

| | |
|---|---|
| N—ethyl 6-[(1,1,3,3-tetramethyl-5-indanyl) carbonyl] 2-naphthalene carboxamide | 0.05 g |
| Isopropyl alcohol | 40.0 g |
| Polymer of acrylic acid, sold under the trade name "CARBOPOL 940" by Goodrich Chemical Co. | 1.0 g |
| Triethanolamine, 99% | 0.6 g |
| Butyl hydroxy anisole | 0.01 g |
| Butyl hydroxy toluene | 0.02 g |
| Tioxolone | 0.5 g |
| Propylene glycol | 8.0 g |
| Purified water, suffcient amount for | 100 g |

In this Example, the active compound can be replaced by the same amount of 6-[(5,5,8,8-tetramethyl-5,6,7,8-tetrahydro-2-naphthyl) hydroxymethyl] 2-naphthalene carboxylic acid or by 0.1 g of N-ethyl 6-[(5,5,8,8-tetramethyl-5,6,7,8-tetrahydro-2-naphthyl) hydroxymethyl] 2-naphthalene carboxamide or even by 0.1 g of 1-(5,5,8,8-tetramethyl-5,6,7,8-tetrahydro-2-naphthyl)-1-(6-carboxy-2-naphthyl) methane.

EXAMPLE 8

Anionic oil-in-water cream

| | |
|---|---|
| 6-[(5,5,8,8-tetramethyl-5,6,7,8-tetrahydro-2-naphthyl) carbonyl] 2-naphthalene carboxylic acid | 0.010 g |
| Sodium dodecyl sulfate | 0.800 g |
| Glycerol | 2.000 g |
| Stearyl alcohol | 20.000 g |
| Triglycerides of capric/caprylic acids, sold under the trade name "Miglyol 812" by Dynamit Nobel | 20.000 g |
| Preservative, sufficient amount | |
| Demineralized water, sufficient amount for | 100.000 g |

EXAMPLE 9

Gel

| | |
|---|---|
| 6-[(5,8-methano-5,6,7,8-tetrahydro-2-naphthyl) carbonyl] 2-napthalene carboxylic acid | 0.050 g |
| Hydroxypropyl cellulose, sold under the trade name "Klucel HF" by Hercules | 2.000 g |
| Water/ethanol, 50:50, sufficient amount for | 100.000 g. |

What is claimed is:

1. A bicyclic naphthalenic compound having the formula

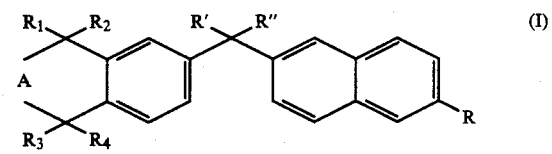 (I)

wherein

A represents methylene or dimethylene, substituted or not by lower alkyl having 1–6 carbon atoms, $R_1$, $R_2$, $R_3$ and $R_4$, each independently, represent hydrogen or lower alkyl having 1–6 carbon atoms, or $R_1$ and $R_3$ taken together form a methylene or dimethylene bridge when A represents dimethylene, R' represents hydrogen, OH, alkoxy having 1–4 carbon atoms, acyloxy having 1–4 carbon atoms or amino, R" represents hydrogen or alkoxy having 1–4 carbon atoms, or R' and R" taken together form an oxo, methano or hydroxyimino group, R represents —CH$_2$OH or —COR$_5$, R$_5$ represents hydrogen, OR$_6$ or

R$_6$ represents hydrogen, alkyl having 1–20 carbon atoms, monohydroxyalkyl, polyhydroxyalkyl, phenyl or phenyl substituted by halogen, —OH, —NO₂, lower alkyl having 1–6 carbon atoms, trifluoromethyl or a carboxylic acid function, benzyl or phenethyl, the residue of glucose, mannose, erythrose or galactose or

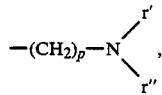

p is 1, 2 or 3, and r' and r", each independently, represent hydrogen, lower alkyl having 1–6 carbon atoms, monohydroxyalkyl, monohydroxyalkyl interrupted by a heteroatom, polyhydroxyalkyl, aryl or benzyl, the residue of an amino acid, an aminoester, glucosamine, galactosamine, mannosamine or meglumine, or r' and r" together with the nitrogen atom to which they are attached, form a heterocycle substituted or unsubstituted, and the salts of said compounds of formula (I) or the optical isomers thereof.

2. The compound of claim 1 wherein said monohydroxyalkyl is 2-hydroxy ethyl, 2-hydroxy propyl or 2'-hydroxy-2-ethoxyethyl.

3. The compound of claim 1 wherein said polyhydroxyalkyl radical is 2,3-dihydroxypropyl, 1,3-dihydroxy-2-propyl or the residue of pentaerythritol.

4. The compound of claim 1 wherein said alkoxy radical is methoxy, isopropoxy, butoxy or tert.butoxy.

5. The compound of claim 1 wherein r' and r" taken together with the nitrogen atom to which they are attached form piperidino, piperazino, morpholino, pyrrolidino or 4-(2'-hydroxyethyl) piperazino.

6. The compound of claim 1 having the formula

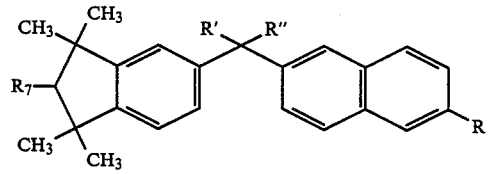

wherein

R' represents hydrogen or OH,

R" represents hydrogen, or

R' and R" taken together form oxo,

R represents CH₂OH or —COOR₆, wherein R₆ represents hydrogen or alkyl having 1–6 carbon atoms, and R₇ represents hydrogen or methyl.

7. The compound of claim 1 having the formula

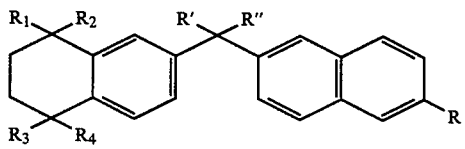

wherein

R₁, R₂, R₃ and R₄ represent —CH₃,

R' represents hydrogen, OH, alkoxy having 1–4 carbon atoms or acyloxy having 1–4 carbon atoms, R" represents hydrogen, or R' and R" taken together form oxo or methano, and R represents —CH₂OH or —COR₅, wherein R₅ represents hydrogen, —OR₆ or

R₆ represents hydrogen or alkyl having 1–6 carbon atoms, and r' and r" represent hydrogen, alkyl having 1–6 carbon atoms, 4-hydroxyphenyl, 2'-hydroxy-2-ethoxyethyl or 1-carboxy-3-methylthiopropyl.

8. The compound of claim 1 having the formula

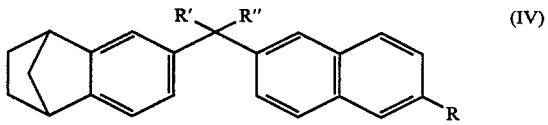

wherein

R' and R" taken together form oxo,

R represents —COR₅,

R₅ represents —OR₆ or

R₆ represents hydrogen or alkyl having 1–6 carbon atoms, and r' and r" represents hydrogen or alkyl having 1–6 carbon atoms.

9. The compound of claim 1 selected from the group consisting of (1) 6-[(1,1,3,3, tetramethyl-5-indanyl) carbonyl] 2-methyl naphthalene carboxylate, (2) 6-[(1,1,3,3, tetramethyl-5-indanyl) carbonyl] 2-naphthalene carboxylic acid, (3) 6-[(1,1,2,3,3, pentamethyl-5-indanyl) carbonyl] 2-methyl naphthalene carboxylate, (4) 6-[(1,1,2,3,3, pentamethyl-5-indanyl) carbonyl] 2-naphthalene carboxylic acid, (5) 6-[(1,1,2,3,3, pentamethyl-5-indanyl) hydroxymethyl] 2-naphthalene carboxylic acid, (6) 6-[(5,5,8,8-tetramethyl-5,6,7,8-tetrahydro-2-naphthyl) hydroxymethyl] 2-naphthalene carboxamide, (7) N-ethyl 6-[(5,5,8,8-tetramethyl-5,6,7,8-tetrahydro-2-naphthyl) hydroxymethyl] 2-naphthalene carboxamide, (8) 1-[(5,5,8,8-tetramethyl-5,6,7,8-tetrahydro-2-naphthyl)-1-(6-carboxy-2-naphthyl) methane, (9) N-ethyl 6-[(1,1,3,3-tetramethyl-5-indanyl) carbonyl] 2-naphthalene carboxamide,

(10) N-ethyl 6-[(1,1,2,3,3-pentamethyl-5-indanyl) carbonyl] 2-napthalene carboxamide,

(11) N-ethyl 6-[(1,1,2,3,3 -pentamethyl-5-indanyl) hydroxymethyl] 2-naphthalene carboxamide,

(12) 6-[(5,5,8,8-tetramethyl-5,6,7,8-tetrahydro-2-naphthyl) acetoxymethyl] 2-napthalene carboxylic acid,

(13) 6-[2-(5,5,8,8-tetramethyl-5,6,7,8-tetrahydro-2-naphthyl) 2-ethenyl] 2-methyl naphthalene carboxylate,

(14) 6-[2-(5,5,8,8-tetramethyl-5,6,7,8-tetrahydro-2-naphthyl)-2-ethenyl] 2-naphthalene carboxylic acid,

(15) 6-[(5,5,8,8-tetramethyl-5,6,7,8-tetrahydro-2-napht-hyl) hydroxymethyl] 2-napthalene carbinol,
(16) 6-[(5,5,8,8-tetramethyl-5,6,7,8-tetrahydro-2-napht-hyl) butoxymethyl] 2-naphthalene carbinol,
(17) 6-[(5,5,8,8-tetramethyl-5,6,7,8-tetrahydro-2-napht-hyl) butoxymethyl] 2-napthalene carboxylic acid,
(18) 6-[(5,5,8,8-tetramethyl-5,6,7,8-tetrahydro-2-napht-hyl) hydroxymethyl] 2-naphthaldehyde,
(19) 6-[(5,5,8,8-tetramethyl-5,6,7,8-tetrahydro-2-napht-hyl) hydroxyiminomethyl] 2-ethyl naphthalene carboxylate,
(20) 6-[(5,5,8,8-tetramethyl-5,6,7,8-tetrahydro-2-napht-hyl) hydroxyiminomethyl] 2-naphthalene carboxylic acid,
(21) N-ethyl 6-[(5,5,8,8-tetramethyl-5,6,7,8-tetrahydro-2-naphthyl) hydroxyiminomethyl] 2-naphthalene carboxamide,
(22) 6-[(5,5,8,8-tetramethyl-5,6,7,8-tetrahydro-2-napht-hyl) aminomethyl] 2-ethyl napthalene carboxylate,
(23) 6-[(5,5,8,8-tetramethyl-5,6,7,8-tetrahydro-2-napht-hyl) aminomethyl] 2-napthalene carboxylic acid,
(24) 6-[(5,5,8,8-tetramethyl-5,6,7,8-tetrahydro-2-napht-hyl) carbonyl] 2-napthalene carboxylic acid and its methyl ester,
(25) N-ethyl 6-[(5,5,8,8-tetramethyl-5,6,7,8-tetrahydro-2-naphthyl) carbonyl] 2-naphthalene carboxamide,
(26) 6-[(5,5,8,8-tetramethyl-5,6,7,8-tetrahydro-2-napht-hyl) carbonyl] 2-naphthalene carboxaldehyde,
(27) 6-[(5,5,8,8-tetramethyl-5,6,7,8-tetrahydro-2-napht-hyl) carbonyl] 2-naphthalene carbinol,
(28) N(2'-hydroxy-2-ethoxyethyl) 6-[5,5,8,8-tetramethyl-5,6,7,8-tetrahydro-2-naphthyl) carbonyl] 2-naphthalene carboxamide,
(29) N-p-hydroxyphenyl 6-[(5,5,8,8-tetramethyl-5,6,7,8-tetrahydro-2-naphthyl) carbonyl] 2-napthalene carboxamide,
(30) N-(1-ethoxycarbonyl-3-methylthiopropyl) 6-[(5,5,8,8-tetramethyl-5,6,7,8-tetrahydro-2-naphthyl) carbonyl] 2-naphthalene carboxamide,
(31) N-(1-carboxy-3-methylthiopropyl) 6-[(5,5,8,8-tetramethyl-5,6,7,8-tetrahydro-2-naphthyl) carbonyl] 2-naphthalene carboxamide,
(32) 6-[(5,8-methano-5,6,7,8-tetrahydro-2-naphthyl) carbonyl] 2-naphthalene carboxylic acid and its methyl ester,
(33) 6-[(5,6,7,8-tetrahydro-2-naphthyl) carbonyl] 2-naphthalene carboxylic acid and its methyl ester, and
(34) N-ethyl 6-[(5,6,7,8-tetrahydro-2-naphthyl) carbonyl] 2-naphthalene carboxamide.

10. A process for preparing the compound of claim 1 comprising reacting in an organic solvent medium under Friedel Crafts reaction conditions an acid chloride of the formula

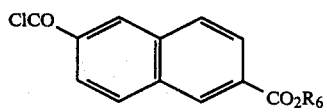

on a naphthalenic compound of the formula

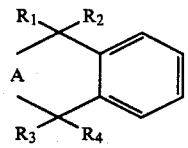

wherein
A, $R_1$ to $R_4$ have the meanings given in claim 1, and $R_6$ is alkyl having 1–20 carbon atoms,
saponifying, if necessary, the resulting keto-ester into the corresponding keto-acid and subsequently transforming said keto-acid into the corresponding amide by reacting said keto-acid with an amine of the formula

wherein r' and r" have the same meanings as given in claim 1 or by transforming said keto-acid into hydroxyacid, methanoacid, hydroxyiminoacid, methylene acid or diol and optionally oxidizing said diol into a corresponding aldehyde alcohol or keto-aldehyde or to the optional transformation thereof into an acyloxy or alkoxy derivative.

11. The process of claim 10 wherein the condensation reaction is carried out in the presence of anhydrous aluminum chloride in 1,2-dichloroethane at a temperature ranging from 0° to 25° C. with stirring.

12. The process of claim 10 wherein the preparation of the amide is carried out in the presence of N,N'-carbonyldiimidazole.

13. The process of claim 10 wherein the reduction of the keto-acid into the corresponding hydroxy acid is effected in the presence of sodium borohydride in tetrahydrofuran.

14. The process of claim 10 wherein the aldehyde alcohol and the keto-aldehyde are obtained by oxidation of the diol with pyridinium chlorochromate, the corresponding diol resulting from the reduction reaction of said keto-acid in the presence of lithium aluminium hydride.

15. The process of claim 10 wherein the compounds of formula (I) wherein R'=R"=H are obtained by reduction with zinc of corresponding ketonic derivatives in acetic acid in the presence of sulfuric acid.

16. The process of claim 10 wherein the compounds of formula (I) wherein R' and R"=methano are obtained by reaction of the correspondiing ketonic compounds with a mixture of triphenylmethyl phosphonium bromide and sodium amide.

17. The process of claim 10 wherein the compounds of formula (I) wherein R' and R"=hydroxyimino are obtained by reaction of ketonic compounds with hydroxylamine hydrochloride in an organic solvent in the presence of a base.

18. A medicine comprising a compound of claim 1 and a pharmaceutically acceptable vehicle.

19. A medicine of claim 18 administered in a daily dosage of about 2 $\mu$g/kg to 2 mg/kg of body weight.

20. A pharmaceutical composition comprising in a pharmaceutically acceptable vehicle suitable for enteral, parenteral, topical or ocular administration, at least one compound of claim 1.

21. The composition of claim 20 provided in a form for topical or ocular administration, said composition containing said compound in an amount ranging from 0.0005 to about 5 percent by weight based on the total weight of said composition.

22. A method for treating a person suffering from a dermotologic, respiratory or opthalomogic disorder comprising administering to said person an effective amount of the composition of claim 20.

23. A cosmetic composition for body or hair hygiene comprising in a cosmetically acceptable vehicle at least one compound of claim 1.

24. A cosmetic composition of claim 23 wherein said compound is present in an amount ranging from 0.0005 to 2 percent by weight based on the total weight of said composition.

25. The cosmetic composition of claim 23 wherein said compound is present in an amount ranging from 0.01 to 1 percent by weight based on the total weight of said composition.

26. N-ethyl 6-[(5,5,8,8-tetramethyl-5,6,7,8-tetrahydro-2-naphthyl) carbonyl] 2-naphthalene carboxamide.

27. A medicine comprising the compound of claim 26 and a pharmaceutically acceptable vehicle.

28. A pharmaceutical composition comprising in a pharmaceutically acceptable vehicle suitable for enteral, parenteral, topical or ocular administration, the compound of claim 26.

29. A method for treating a person suffering from a dermatologic, respiratory or ophthalomogic disorder comprising administering to said person an effective amount of the composition of claim 28.

30. A cosmetic composition for body or hair hygiene comprising in a cosmetically acceptable vehicle the compound of claim 26.

* * * * *